(12) United States Patent
Abel et al.

(10) Patent No.: US 9,937,140 B2
(45) Date of Patent: Apr. 10, 2018

(54) BRANCHED CHAIN AMINO ACIDS: FORMULATIONS AND METHODS OF TREATMENT

(71) Applicant: The University of Utah Research Foundation, Salt Lake City, UT (US)

(72) Inventors: Evan Dale Abel, Coralville, IA (US); Christian Michael Riehle, Offenburg (DE)

(73) Assignee: University of Utah Research Foundation, Salt Lake City, UT (US)

( * ) Notice: Subject to any disclaimer, the term of this patent is extended or adjusted under 35 U.S.C. 154(b) by 262 days.

(21) Appl. No.: 14/212,939

(22) Filed: Mar. 14, 2014

(65) Prior Publication Data

US 2015/0126604 A1 May 7, 2015

Related U.S. Application Data

(60) Provisional application No. 61/784,939, filed on Mar. 14, 2013.

(51) Int. Cl.
*A61K 31/198* (2006.01)
*A61K 9/00* (2006.01)
*A61K 9/19* (2006.01)

(52) U.S. Cl.
CPC .......... *A61K 31/198* (2013.01); *A61K 9/0019* (2013.01); *A61K 9/19* (2013.01)

(58) Field of Classification Search
CPC ....... A61K 31/198; A61K 9/0019; A61K 9/19
See application file for complete search history.

(56) References Cited

U.S. PATENT DOCUMENTS 5,767,123 A * 6/1998 Yoshida .................. A23L 1/302
514/276

FOREIGN PATENT DOCUMENTS

WO    WO 2006127761 A1 * 11/2006 ............. A23L 1/296

OTHER PUBLICATIONS

Effects of Intraperitoneal L-Leucine, L-Isoleucine, L-Valine, and L-Arginine on Milk Fat Depression in Early Lactation Cows, A. Hopkins, A. H. Rakes, T. E. Daniel, C. A. Zimmerman, and W. J. Croom, Jr., Journal of Dairy Science vol. 77, Issue 4, Apr. 1994, pp. 1084-1092.*
M. Korhonen, A. Vanhatalo, and P. Huhtanen, Evaluation of Isoleucine, Leucine, and Valine as a Second-Limiting Ammo Acid for Milk Production in Dairy Cows Fed Grass Silage Diet, J. Dairy Sci. 85:1533-1545.*
Hara et al., "Amino Acid Sufficiency and mTOR Regulate p70 S6 Kinase and eIF-4E BP1 through a Common Effector Mechanism", The Journal of Biological Chemistry, vol. 273, No. 23, Issue of Jun. 5, pp. 14484-14494, 1998.
Ohashi et al., "Effects of Supplementation with Branched-Chain Amino Acids on Protein-Nutritional Status in Rats Treated by Carbon Tetrachloride", Nihon Shokakibyo Gakkai Zasshi. Aug. 1989; 86(8):1645-53.

* cited by examiner

*Primary Examiner* — Sarah Pihonak
*Assistant Examiner* — Jason Deck

(57) ABSTRACT

The present disclosure includes a formulation of branched chain amino acids and arginine for treatment of diseases for which the pathological mechanism includes autophagy. The formulation includes defined ratios of the branched chain amino acids Isoleucine, Leucine, and Valine along with Arginine. These disease indications include congestive heart failure, myocardial infarction, and ischemia reperfusion injury. Diseases of other organs that involve autophagy are also disclosed. Additionally, methods of using the disclosed formulation to treat these disease indications are provided. The disclosure also describes a kit that includes a lyophilized form of the formulation, a solvent for reconstitution, and instructions directing reconstitution.

10 Claims, 18 Drawing Sheets

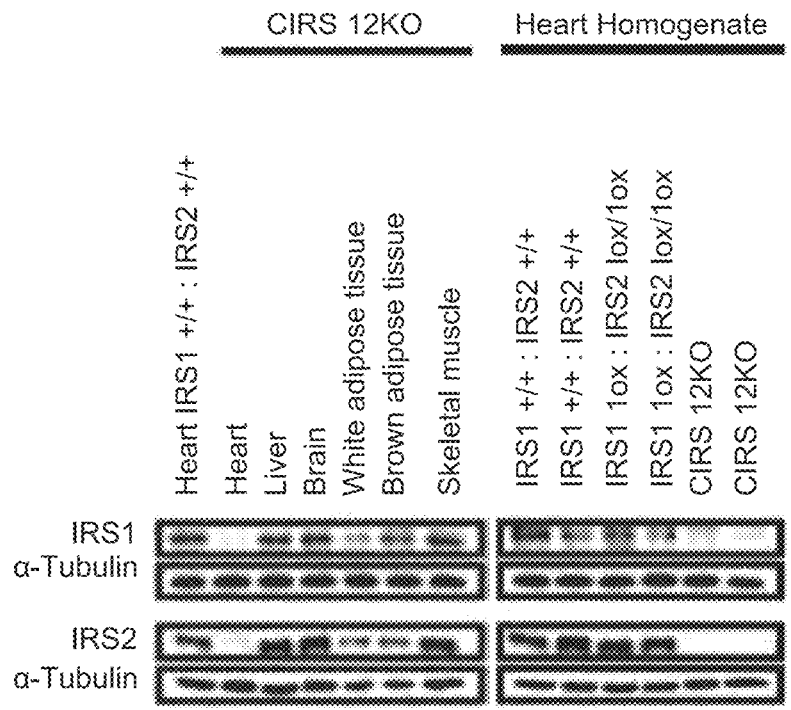
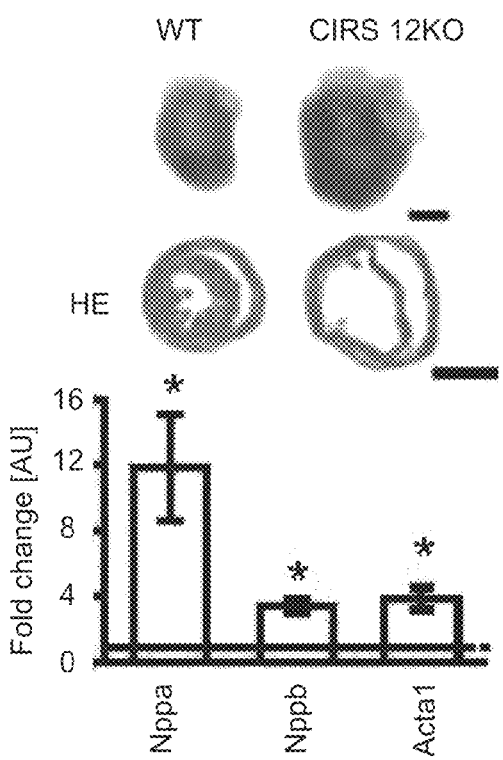
FIG 1A
FIG 1B
FIG 1C

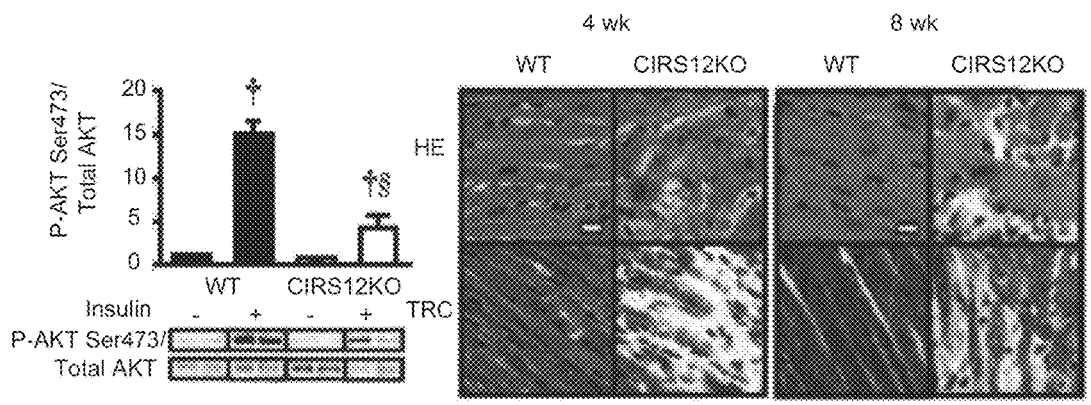
FIG 1D                    FIG 1E
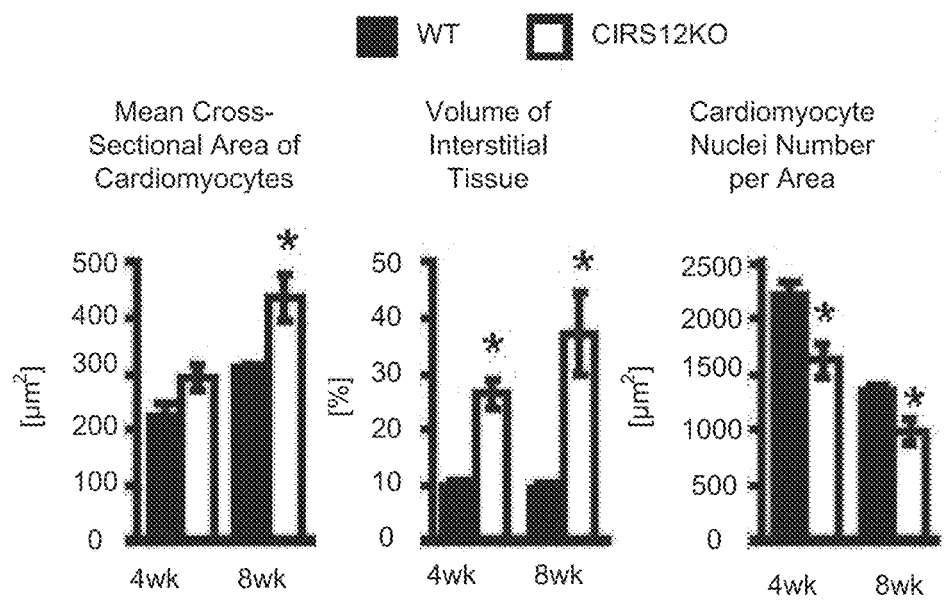
FIG 1F          FIG 1G          FIG 1H

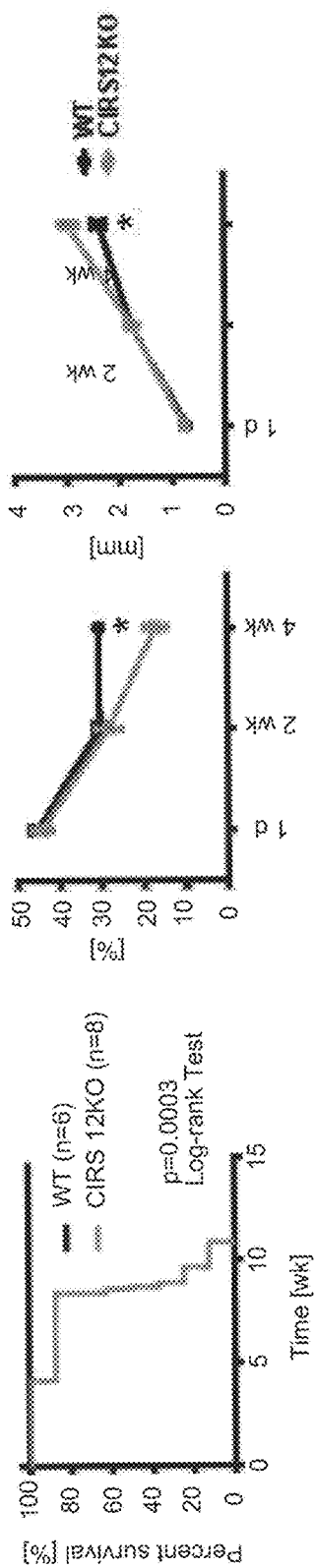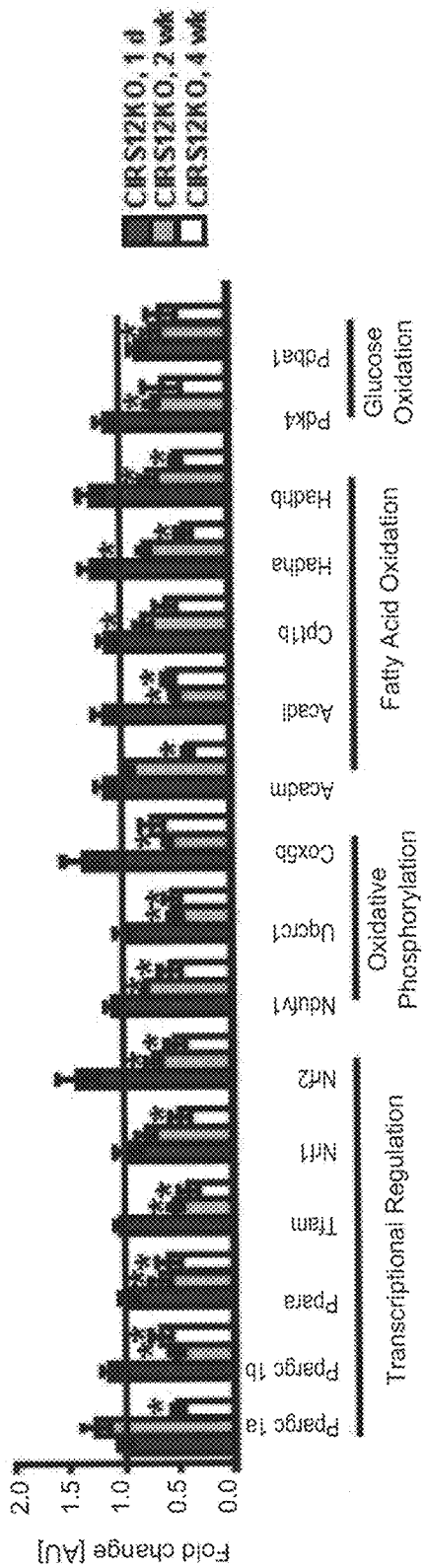
FIG 1J
FIG 1K
FIG 1L
FIG 1M

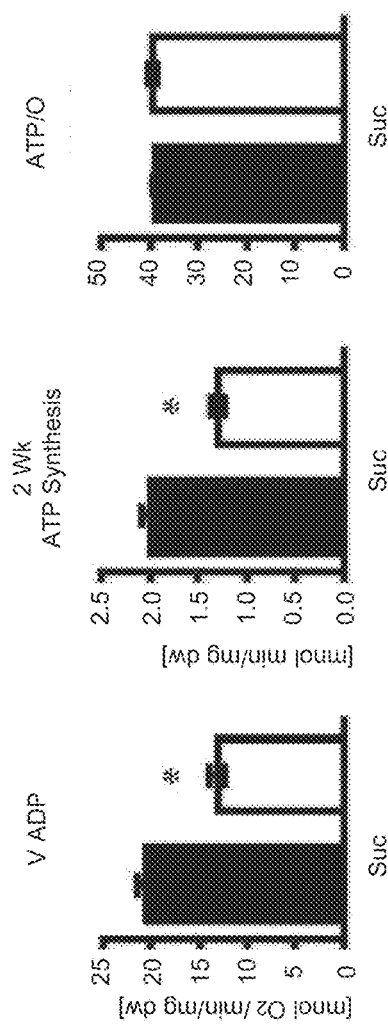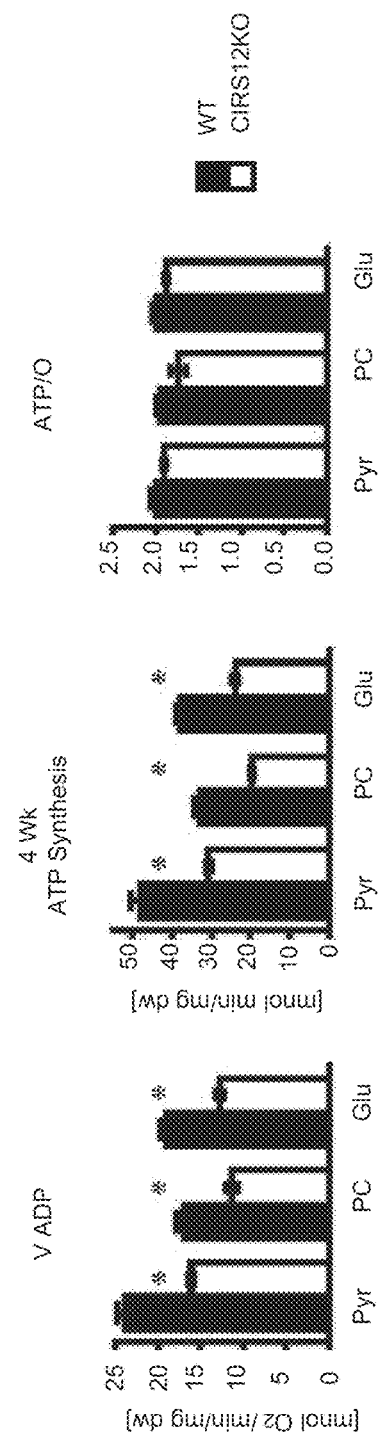

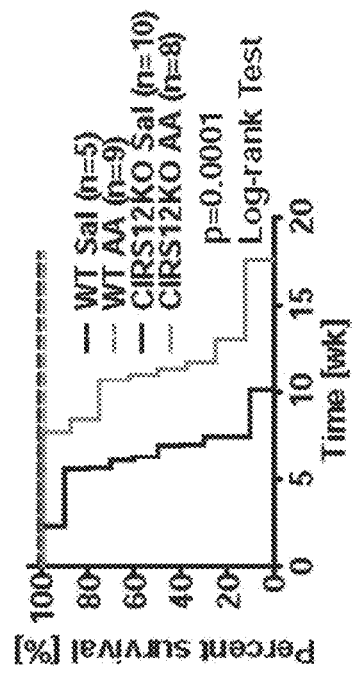
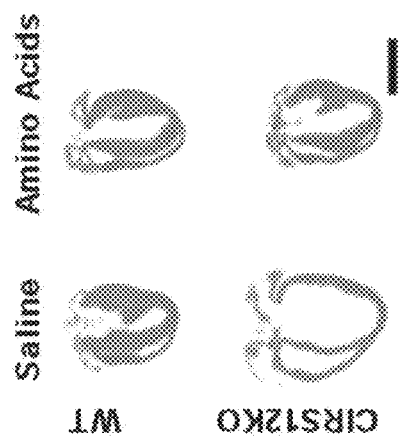
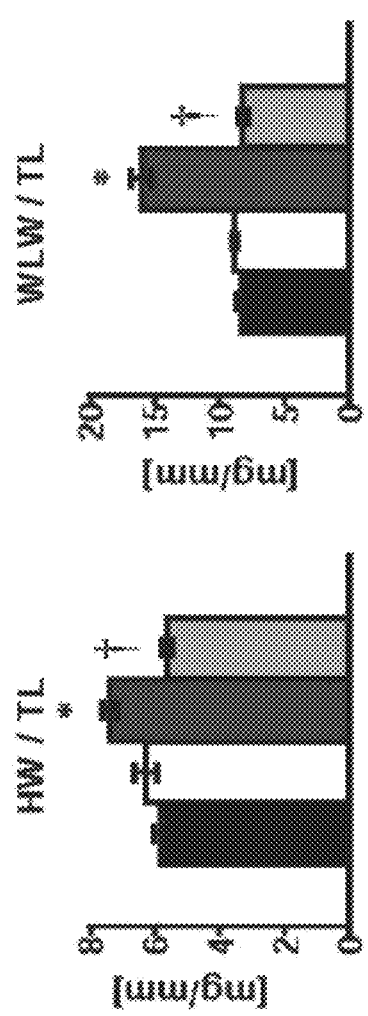

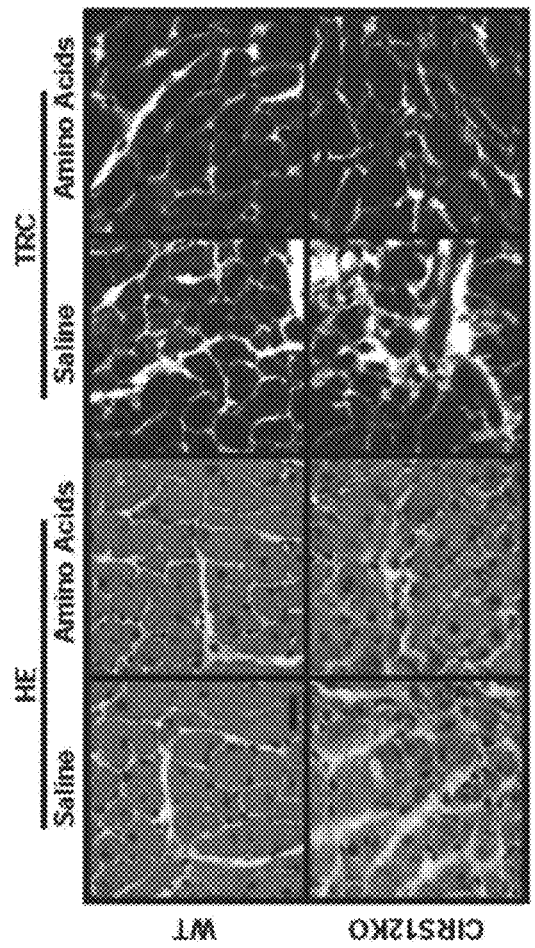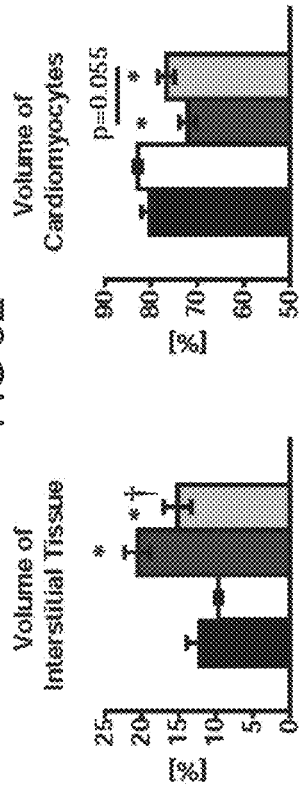
FIG 3E
FIG 3F
FIG 3G

■ WT Sal  □ WT AA  ■ CIRS12KO Sal  ▨ CIRS12KO AA

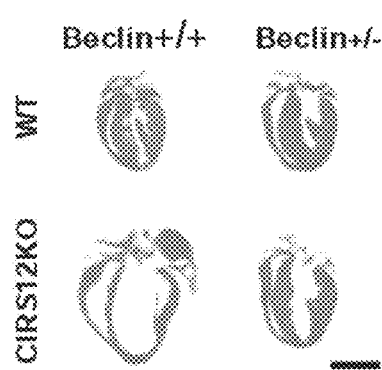
FIG 4A
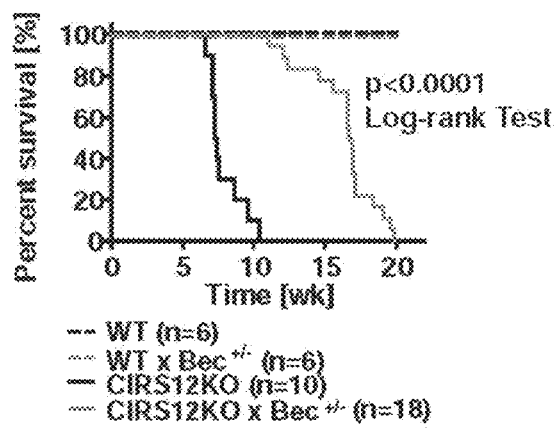
FIG 4B
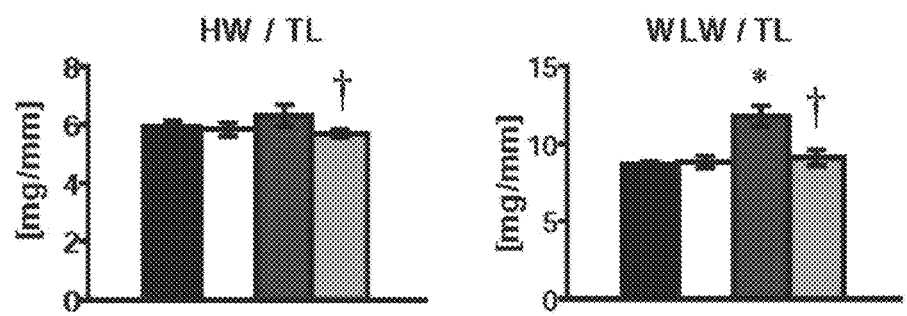
FIG 4C
FIG 4D
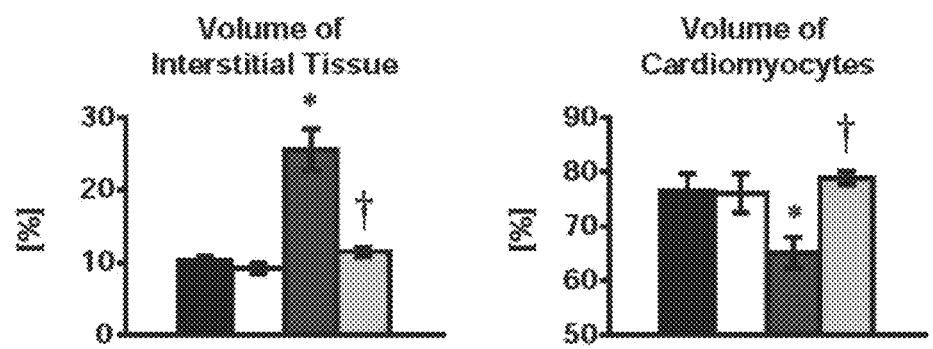
FIG 4E
FIG 4F

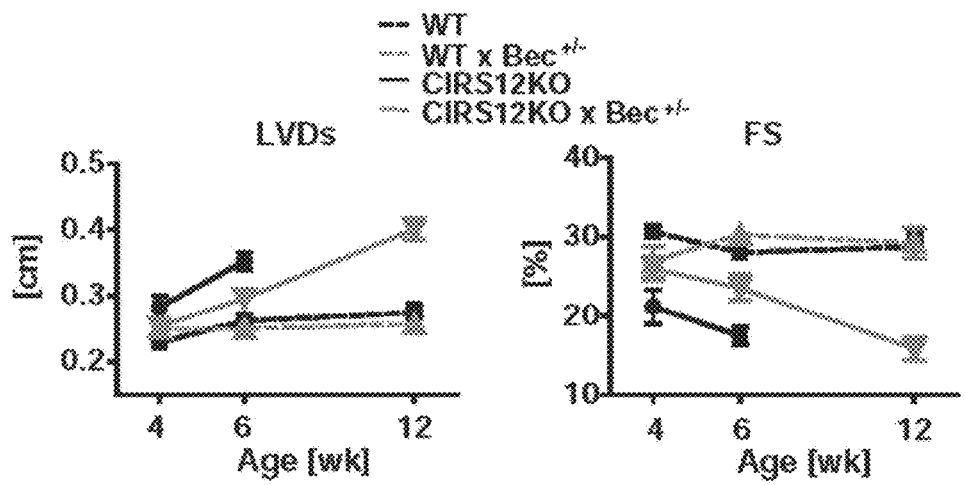
FIG 4G   FIG 4H
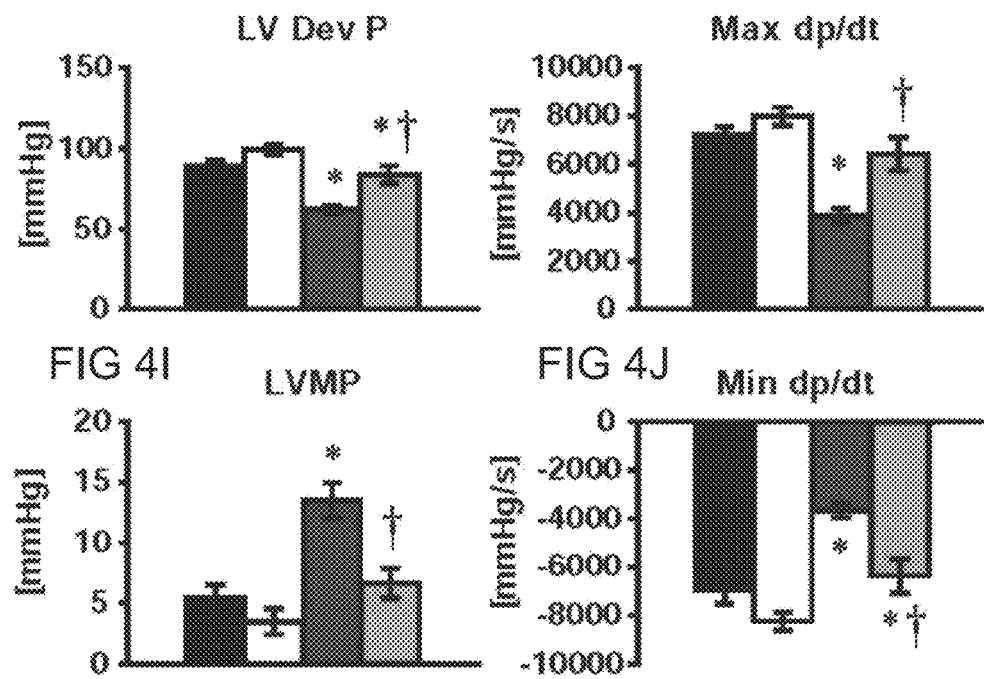
FIG 4I   FIG 4J
FIG 4K   FIG 4L

BRANCHED CHAIN AMINO ACIDS: FORMULATIONS AND METHODS OF TREATMENT

RELATED APPLICATION

The present application claims priority to U.S. provisional application Ser. No. 61/784,939, titled "Branched Chain Amino Acids: Formulations and Methods of Treatment," filed Mar. 14, 2013. This application is hereby incorporated by reference in its entirety.

STATEMENT REGARDING FEDERALLY SPONSORED RESEARCH

This invention was made with government support under grants RO1 DK092065, RO1HL070070, RO1HL108379 UO1HL087947 awarded by the NIH. The government has certain rights in the invention.

FIELD OF THE INVENTION

The present invention provides formulations for branched chain amino acids and methods of using the formulations to treat or prevent heart failure, ischemia reperfusion injury, and diseases of other organs in which autophagy is included in the pathological mechanism.

BACKGROUND

Autophagy is a conserved cellular process that is activated under conditions of nutrient stress to promote cell survival. The induction of autophagy in the heart, liver and diaphragms of mammals in the perinatal period is an essential adaptation that is required to survive early neonatal starvation. Constitutive levels of autophagy are low during embryogenesis but are significantly induced after birth and maintain organ function in the postnatal starvation period until a consistent nutrient supply is restored via the maternal milk supply and insulin levels rise. Excessive and long-term induction of autophagy may ultimately lead to destruction of essential proteins and organelles, which beyond a certain threshold results in cell death. The mechanisms that mediate the suppression of autophagy once feeding is established are not known. Furthermore, methods of inhibiting autophagy would be useful to treat or prevent heart failure, myocardial infarction, ischemia reperfusion injury, and diseases of other organs in which autophagy is included in the disease processes of both infants and adults.

BRIEF SUMMARY

The present disclosure relates to formulations of L-isoleucine, L-leucine, L-valine, L-arginine in defined relative ratios and in a solution of a defined osmolality that are useful to treat a disease or condition for which pathological autophagy is a component of the pathological process. These diseases include autophagy of the heart, congestive heart failure, cardiomyopathy, myocardial infarction and ischemia reperfusion injury.

Further disclosed herein is a lyophilized preparation of the amino acid formulation. Such a preparation could be resuspended in an appropriate solvent prior to administering to a human or animal in need thereof.

Also disclosed herein is a kit comprising the lyophilized preparation of the amino acid formulation, a solvent for reconstituting the lyophilized preparation, and instructions for directing reconstitution. The kit may also include an injection device.

Also disclosed herein are methods of using the disclosed amino acid formulations to treat the diseases for which the amino acid formulations are useful. These methods may be used to treat adult and infant humans and animals both as a prophylactic for those at risk of developing the relevant disease indications for which the formulation is useful and as a therapeutic for those suffering from such diseases. Methods of use include intravenous and intraperitoneal injection and oral administration.

BRIEF DESCRIPTION OF THE FIGURES

FIG. 1A shows representative immunoblots for IRS1 and IRS2 in ventricular homogenates of various tissues and ventricular homogenates from four-week-old mice with genotypes as indicated.

FIG. 1B shows representative photographs and Hematoxylin/Eosin (HE) stained sections from wild type and CIRS12KO hearts (4 weeks of age), scale bars=2 mm.

FIG. 1C is a graphical representation of a northern blot signal showing increased mRNA-expression of heart failure/hypertrophy markers at the age of 4 weeks (normalized to Cphn, n=8).

FIG. 1D is an immunoblot and graphical representation of the immunoblot signal measuring phosphorylation of Akt (Ser473) in ventricle homogenates from four-week-old wild type and CIRS12KO mice.

FIG. 1E shows representative Hematoxylin/Eosin (HE) and Trichrome (TRC) stains (n=3-6) of heart tissues from four-week-old and eight-week-old mice of the indicated genotypes.

FIG. 1F is a stereological analysis of the tissue in FIG. 1E showing a quantification of mean cross sectional area of cardiomyocytes.

FIG. 1G a stereological analysis of the tissue in FIG. 1E showing a quantification of volume of interstitial tissue.

FIG. 1H a stereological analysis of the tissue in FIG. 1E showing a quantification of cardiomyocyte nuclei number.

FIG. 1J is a graph representing survival of CIRS12KO mice and wild type controls.

FIG. 1K is a graphical representation of a time course for fractional shortening (FS), at systole (n=4-15).

FIG. 1L is a graphical representation of a time course for left ventricular cavity diameter at systole (LVDs) (n=4-15).

FIG. 1M is a graphical representation of mRNA levels of the indicated transcripts.

FIG. 1N is a graphical representation of ADP-stimulated mitochondrial oxygen consumption (VADP) in cardiac fibers from two-week-old CIRS12KO mice with Succinate/Rotenone as substrate (n=6).

FIG. 1O is a graphical representation of ADP-stimulated ATP-production in tissues as described in FIG. 1N.

FIG. 1P is a graphical representation of ATP/O ratios in tissues as described in FIGS. 1N and 1O. ATP/O ratios were the same in both genotypes.

FIG. 1Q is a graphical representation of VADP respiration for Pyruvate (Pyr), Palmitoyl-Carnitine (PC), and Glutamate (Glu) each combined with malate as substrate in fibers obtained from CIRS12KO hearts at 4 weeks of age (n=6).

FIG. 1R is a graphical representation of ATP synthesis in tissues as described in FIG. 1Q.

FIG. 1S is a graphical representation of ATP/O ratios synthesis in tissues as described in FIGS. 1Q and 1R.

FIG. 3A shows representative Hematoxylin/Eosin (HE) stains from wild type and CIRS12KO hearts (6 wk. of age) following saline or BCAA/Arg treatment (scale bars=3 mm).

FIG. 3B is a graph illustrating a survival curve of CIRS12KO and wild type controls following Saline (Sal) and BCAA/Arg (AA) treatment. BCAA/Arg supplementation increased the average lifespan of CIRS12KO mice from 6.6 to 11.1 weeks (p=0.0001, Log-rank Test).

FIG. 3C is a graph illustrating the ratio of heart weight to tibia length (HW/TL) in CIRS12KO mice and wild type controls following saline or BCAA/Arg treatment.

FIG. 3D is a graph illustrating ratio of wet lung weight to tibia length (WLW/TL) in CIRS12KO mice and wild type controls following saline or BCAA/Arg treatment.

FIG. 3E shows representative Hematoxylin/Eosin (HE) and Trichrome (TRC) staining of hearts of CIRS12KO mice and wild type controls following saline or BCAA/Arg treatment (scale bars=20 μm, n=6-7).

FIG. 3F is a graph illustrating a stereological analysis of tissues shown in FIG. 3E. The bars represent volume of interstitial tissue.

FIG. 3G is a graph illustrating a stereological analysis of tissues shown in FIG. 3E. The bars represent volume of cardiomyocytes.

FIG. 4A shows representative Hematoxylin/Eosin (HE) stains of heart tissue from wild type and CIRS12KO mice (6 wk. of age) expressing Beclin+/+ or Beclin+/− alleles (scale bars=3 mm).

FIG. 4B is a graph illustrating a survival curve of CIRS12KO and wild type control mice expressing Beclin+/+ or Beclin+/− alleles.

FIG. 4C is a graph illustrating heart weight to tibia length (HW/TL) ratios in mice with the indicated genotypes.

FIG. 4D is a graph illustrating wet lung weight to tibia length (WLW/TL) ratios in mice with the indicated genotypes.

FIG. 4E is a graph illustrating a stereological analysis of representative Hematoxylin/Eosin (HE) and Trichrome (TRC) staining in hearts from 6-week-old mice. Volume of interstitial tissue is quantified.

FIG. 4F is a graph illustrating volume of cardiomyocytes in tissues described in FIG. 4E.

FIG. 4G is a graph illustrating a time course for left ventricular cavity diameter at systole (LVDs) in mice with the indicated genotype (n=5-10).

FIG. 4H is a graph illustrating fractional shortening (FS) in mice described in FIG. 4E.

FIG. 4I is a graph illustrating invasive measurement of left ventricular developed pressure (LV Dev P) at six weeks of age as assessed by catheterization.

FIG. 4J is a graph illustrating invasive measurement of maximal rate of decrease in left ventricular pressure (Max dp/dt) in mice described in FIG. 4H.

FIG. 4K is a graph illustrating invasive measurement of left ventricular minimum pressure (LVMP) in the mice described in FIG. 4H.

FIG. 4L is a graph illustrating invasive measurement of minimal rate of increase in left ventricular pressure (Min dp/dt) in mice described in FIG. 4H.

DETAILED DESCRIPTION

Figure 1I:
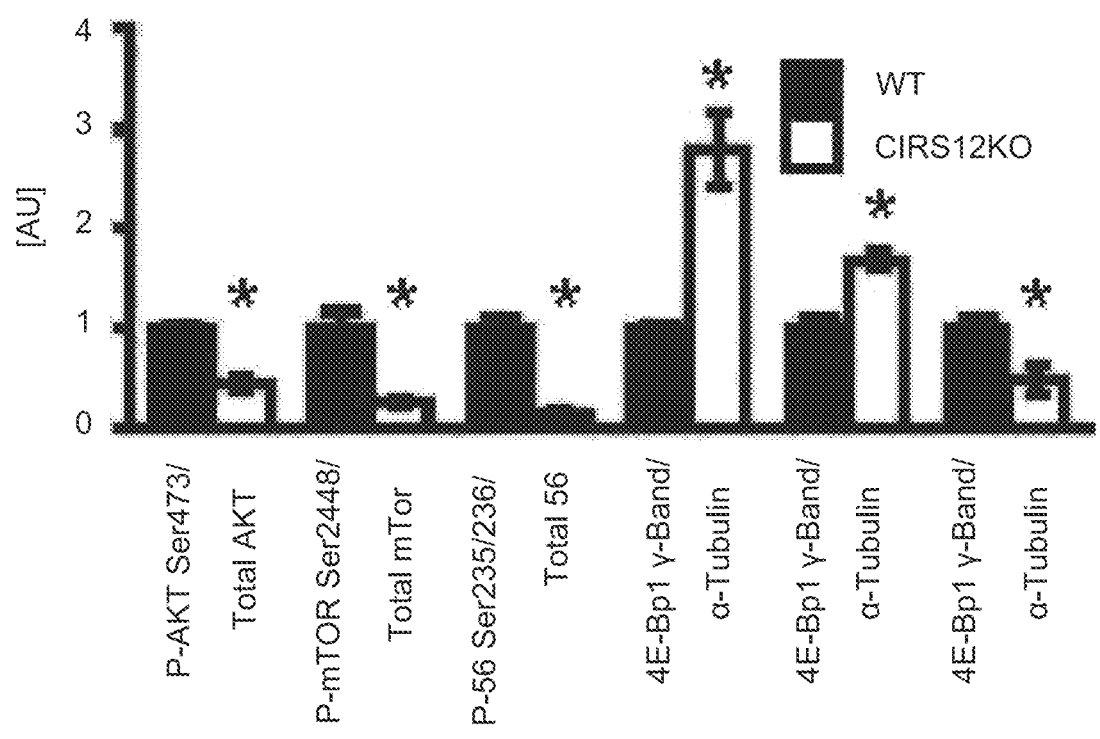
FIG. 1I is a graphical representation of signal from an immunoblot showing diminished phosphorylation of IRS1/2 downstream targets in 1 day old CIRS12KO hearts.

The present disclosure relates to a formulation that comprises branched chain amino acids L-isoleucine, L-leucine, and L-valine, combined with L-arginine (hereinafter, "BCAA/Arg") that are useful for the treatment of diseases for which the pathological mechanism includes autophagy and methods of using the BCAA/Arg formulations to treat such diseases.

The branched chain amino acid formulation includes relative ratios of the amino acids that are unique to the present disclosure. The relative ratios of L-isoleucine, L-leucine, and L-valine are about 1:2:1.2 with the relative ratio of each amino acid being plus or minus 0.2. Specifically, the relative ratios of L-isoleucine, L-leucine, and L-valine may be 1(+/−0.2):2(+/−0.2):1.2 (+/−0.2). In one embodiment, the relative ratios of L-isoleucine, L-leucine, and L-valine may be +/−0.1 such as 1(+/−0.1):2(+/−0.1):1.2 (+/−0.1). In another embodiment disclosed herein, the formulation includes arginine and the relative ratios of L-isoleucine, L-leucine, L-valine, and arginine are about 1:2:1.2:1. As with the relative ratios of branched chain amino acids L-isoleucine, L-leucine, and L-valine, the relative ratio of arginine may be +/−0.2, including +/−0.1.

In a one embodiment, the BCAA/Arg formulation comprises L-isoleucine in a concentration of about 6 (+/−0.3) g/L, L-leucine in a concentration of about 12 (+/−0.3) g/L, and L-valine in a concentration of about 7.2 (+/−0.3) g/L. In another embodiment, the BCAA/Arg formulation comprises L-isoleucine in a concentration of about 6 (+/−0.2) g/L, L-leucine in a concentration of about 12 (+/−0.2) g/L, and L-valine in a concentration of about 7.2 (+/−0.2) g/L.

In another embodiment, the BCAA/Arg formulation comprises L-isoleucine in a concentration of about 6 g/L, L-leucine in a concentration of about 12 g/L, L-valine in a concentration of about 7.2 g/L, and L-arginine is present in a concentration of about 6.04 g/L.

In one embodiment disclosed herein, the pH of the BCAA/Arg formulation is a physiologically tolerable pH. In another embodiment, the formulation is within a pH range of from about 6.9 to about 7.8. In still another embodiment, the formulation is within a pH range of from about 7.1 to about 7.6. In another embodiment the BCAA/Arg formulation is about pH 7.4.

The embodiments of the BCAA/Arg formulation, as disclosed herein, have an osmolarity that results in a solution that may safely be administered in relatively large volumes. The osmolarity may be within a range of about 300 to about 325. In another embodiment, the osmolarity is within a range of about 305 to about 320. In still another embodiment, the osmolarity is within a range of about 310 to about 315. In another embodiment, the osmolarity is about 313 mosm (mOsmol/L). An embodiment of the BCAA/Arg formulation of about 313 mosm and about pH 7.4 was tolerated in mice at a dose of up to about 10% of the body weight/day via intraperitoneal injections. This is near the plasma osmolarity, which may be well tolerated by minimizing the osmotic shift of plasma water. Consequently, high volumes of the BCAA/Arg formulation may be safely administered.

In contrast, intraperitoneal injections of other amino acid mix solutions which were prepared according to commercially available solutions, including Aminoleban® (768 mosm; Ile, 9 g/L; Leu, 11 g/L; Val, 8.4 g/L; Arg, 7.3 g/L), caused increased mortality in mice. This may be due, at least in part, to the elevated osmolarity of the solution relative to that of the present invention. Furthermore, the commercially available solutions provided no beneficial effect to a mouse model of heart failure (CIRS12KO mice, described below).

The pH of the BCAA/Arg formulation may be maintained with a physiologically tolerable buffer. In one embodiment, the buffer is a phosphate buffer.

The BCAA/Arg formulation may be provided in an aqueous solution. In one embodiment, the aqueous solution is sterile and pyrogen-free. In an alternative embodiment, the BCAA/Arg formulation is in a lyophilized form. The lyophilized form of the BCAA/Arg formulation may be provided in a vial, ampoule, or other container and reconstituted with an aqueous solution, including, but not limited to, sterile water.

In an embodiment disclosed herein, the BCAA/Arg formulation is provided as a kit. The kit may comprise the BCAA/Arg formulation in lyophilized form, along with a vial, ampoule, bottle, or other container of sterile water, and instructions directing reconstitution of the BCAA/Arg formulation with the sterile water provided in the kit. The kit may also include an injection device for administering the reconstituted BCAA/Arg formulation.

While myocardial autophagy is an evolutionary mechanism that allows neonates to survive short-term nutrient deprivation immediately after birth, this process is also part of the pathological processes of heart disease including congestive heart failure, myocardial infarction, and ischemia reperfusion injury. Diseases of other organs also involve autophagy. These include neurodegenerative diseases such as Alzheimer's disease, Huntington's disease, transmissible spongiform encephalopathies, and Parkinson's disease. Autophagy is also thought to play a role in liver diseases, such as α1-antitrypsin deficiency, and in myodegenerative diseases, such as Danon disease, and in diabetes.

In one embodiment disclosed herein, methods are provided to administer the BCAA/Arg formulation to treat these and other diseases in which autophagy is involved. Throughout this specification, the terms "treat" and "treatment" mean both administering as a therapeutic and as a prophylactic. Thus, the methods disclosed herein are representative embodiments of methods that are useful to both prevent disease and to mitigate or reverse an ongoing disease process.

The present disclosure further relates to methods of using BCAA/Arg formulations to treat diseases for which the pathological mechanism includes autophagy. As described above, these include congestive heart failure, myocardial infarction, ischemia reperfusion injury and diseases of organs other than heart that include pathological autophagy such as neurodegenerative diseases and diabetes.

The methods include administration of the BCAA/Arg formulation by injection, including, but not limited to, intraperitoneal and intravenous injection. Methods of administering the BCAA/Arg formulation orally are also provided herein.

Materials and Methods

Mice

CIRS12KO (IRS1lox/lox:IRS2lox/lox:αMHC-Cre+/−) mice were generated by breeding IRS1lox/lox:IRS2lox/10× with αMHC-Cre+/− in order to obtain IRS1+/lox:IRS2+/lox:αMHC-Cre+/−. CIRS12KO were obtained by crossing IRS1lox/lox:IRS2lox/10× with IRS1+/lox:IRS2+/lox:αMHC-Cre+/−. CIRS12KO×Beclin+/− were bred in analogous manner. The generation of transgenic mice for IRS1lox/lox, IRS2lox/lox, αMHC-Cre+/−, and Beclin+/− has been previously described in the art. Wild type controls for CIRS12KO (indicated as WT) harbored homozygous floxed alleles for both IRS1 and IRS2 in the absence of αMHC-Cre. Mice expressed both alleles for Beclin unless otherwise indicated. Genotyping of mice was performed as previously described in the art. All mice were maintained on a C57/BL6/129Sv mixed genetic background. Animals were housed with a 12 h light/12 h dark cycle at 22° C. with free access to food and water. All experiments were performed in accordance with protocols approved by the Institutional Animal Care and Use Committee of the University of Utah.

RNA Extraction and Quantitative RT-PCR

Total RNA was extracted from hearts with TRIzol reagent (Invitrogen Corporation, Carlsbad, Calif.), purified with the RNeasy kit (Qiagen Inc., Valencia, Calif.) and reverse transcribed. Quantitative real-time PCRs were performed using SYBR Green I and ROX internal reference. Primer sequences and accession numbers are listed in Table 1 below.

TABLE 1

Primer Sequences Used for Quantification of mRNA Levels by RT-PCR

Gene Name
Gene Sequence of forward and reverse primers (5'→3')
GenBank Accession Number Actin, alpha 1, skeletal muscle (Acta1)
CCTGTATGCCAACAACGTCA (SEQ ID NO: 1)
CTCGTCGTACTCCTGCTTGG (SEQ ID NO: 2)
XM_134551

Acyl-Coenzyme A dehydrogenase, long-chain (Acadl)
ATGGCAAAATACTGGGCATC (SEQ ID NO: 3)
TCTTGCGATCAGCTCTTTCA (SEQ ID NO: 4)
NM_007381

Acyl-Coenzyme A dehydrogenase, medium chain (Acadm)
ACTGACGCCGTTCAGATTTT (SEQ ID NO: 5)
GCTTAGTTACACGAGGGTGATG (SEQ ID NO: 6)
NM_007382

BCL2/adenovirus E1B interacting protein 3 (Bmp3)
TTGGCGAGAAAAACAGCAC (SEQ ID NO: 7)
GCTGAGAAAATTCCCCCTTT (SEQ ID NO: 8)
NM_009760

Carnitine palmitoyltranferase 1b, muscle (Cpt1b)
TGCCTTTACATCGTCTCCAA (SEQ ID NO: 9)
AGACCCCGTAGCCATCATC (SEQ ID NO: 10)
NM_009948

Cyclophilin A (Cphn)
AGCACTGGAGAGAAAGGATTTGG (SEQ ID NO: 11)
TCTTCTTGCTGGTCTTGCCATT (SEQ ID NO: 12)
NM_008907

Cytochrome c oxidase subunit IV isoform 1 (Cox4i1)
CGCTGAAGGAGAAGGAGAAG (SEQ ID NO: 13)
GCAGTGAAGCCAATGAAGAA (SEQ ID NO: 14)
NM_009941

Cytochrome c oxidase, subunit Vb (Cox5b)
TGGAGGTGGTGTCCCTACTG (SEQ ID NO: 15)
CTCTTGTTGCTGATGGATGG (SEQ ID NO: 16)
M_009942

Estrogen related receptor alpha (Esrra)
GGAGGACGGCAGAAGTACAA (SEQ ID NO: 17)
CAGGTTCAACAACCAGCAGA (SEQ ID NO: 18)
NM_007953

Eukaryotic translation initiation factor 4E (Eif4e)
AGGTGGGCACTCTGGTTTTT (SEQ ID NO: 19)
ATAGGCTCAATCCCGTCCTT (SEQ ID NO: 20)
NM_007917

Eukaryotic translation initiation factor 4E binding protein 1 (Eif4ebp1)
CGTAGGACGCAATGATGCT (SEQ ID NO: 21)
TGTTCACAAAATTCAAGGCAGA (SEQ ID NO: 22)
NM_007918

Fatty acid binding protein 3 (Fabp3)
GACGGGAAACTCATCCTGAC (SEQ ID NO: 23)
TCTCCAGAAAAATCCCAACC (SEQ ID NO: 24)
NM_010174.1

F-box protein 32 (Fbxo32)
GCTGGATTGGAAGAAGATGTATT (SQ ID NO: 25)
TTGAGGGGAAAGTGAGACG (SEQ ID NO: 26)
NM_026346

TABLE 1 -continued

Primer Sequences Used for Quantification of mRNA Levels by RT-PCR

Gamma-aminobutyric acid (GABA) A receptor-associated
protein-like 1 (Gabarapl1)
CTTCCACCCAGGCTTCATAG (SEQ ID NO: 27)
TATGGGATGAGGAGCAGGAC (SEQ ID NO: 28)
NM_020590

Gamma-aminobutyric acid receptor associated protein (Gabarap)
CGGATAGGAGACCTGGACAA (SEQ ID NO: 29)
ACTGGTGGGTGGAATGACA (SEQ ID NO: 30)
NM_019749

Hydroxyacyl-CoA Dehydrogenase-alpha subunit (Hadha)
TCAGGAGGGCTCAAAGAATAA (SEQ ID NO: 31)
GAAAGCCAAGCCCAAAGAC (SEQ ID NO: 32)
XM_131963

Hydroxyacyl-Coenzyme A dehydrogenase-beta sububit (Hadhb)
GCCAACAGACTGAGGAAGGA (SEQ ID NO: 33)
ACACTGGCAAGGCTGGATT (SEQ ID NO: 34)
NM_145558

Microtubule-associated protein 1 light chain 3 beta (Map1lc3b)
CGTCCTGGACAAGACCAAGT (SEQ ID NO: 35)
ATTGCTGTCCCGAATGTCTC (SEQ ID NO: 36)
NM_026160

NADH dehydrogenase (ubiquinone) 1 alpha subcomplex, 9 (Ndufa9)
ATCCCTTACCCTTTGCCACT (SEQ ID NO: 37)
CCGTAGCACCTCAATGGACT (SEQ ID NO: 38)
NM_025358

NADH dehydrogenase (ubiquinone) flavoprotein 1 (Ndufv1)
TGTGAGACCGTGCTAATGGA (SEQ ID NO: 39)
CATCTCCCTTCACAAATCGG (SEQ ID NO: 40)
NM_133666

Natriuretic peptide precursor type A (Nppa)
ATGGGCTCCTTCTCCATCA (SEQ ID NO: 41)
CCTGCTTCCTCAGTCTGCTC (SEQ ID NO: 42)
K02781

Natriuretic peptide precursor type B (Nppb)
GGATCTCCTGAAGGTGCTGT (SEQ ID NO: 43)
TTCTTTTGTGAGGCCTTGGT (SEQ ID NO: 44)
D16497

Nuclear respiratory factor 1 (Nrf1)
CTTCAGAACTGCCAACCACA (SEQ ID NO: 45)
GCTTCTGCCAGTGATGCTAC (SEQ ID NO: 46)
NM_010938

Nuclear respiratory factor 2 (Nrf2)
AGTCTTCACTGCCCCTCATC (SEQ ID NO: 47)
TCTGTCAGTGTGGCTTCTGG (SEQ ID NO: 48)
NM_010902

Peroxisome proliferative activated receptor, gamma,
coactivator 1 alpha (Ppargc1a)
GTAAATCTGCGGGATGATGG (SEQ ID NO: 49)
AGCAGGGTCAAAATCGTCTG (SEQ ID NO: 50)
NM_008904

Peroxisome proliferative activated receptor, gamma,
coactivator 1 beta (Ppargc1b)
TGAGGTGTTCGGTGAGATTG (SEQ ID NO: 51)
CCATAGCTCAGGTGGAAGGA (SEQ ID NO: 52)
NM_133249

Peroxisome proliferator activated receptor alpha (Ppara)
GAGAATCCACGAAGCCTACC (SEQ ID NO: 53)
AATCGGACCTCTGCCTCTT (SEQ ID NO: 54)
NM_01114

Phosphoinositide-3-kinase, class 3 (Pik3c3)
TGTCAGATGAGGAGGCTGTG (SEQ ID NO: 55)
CCAGGCACGACGTAACTTCT (SEQ ID NO: 56)
NM_181414

TABLE 1 -continued

Primer Sequences Used for Quantification of mRNA Levels by RT-PCR

```
Pyruvate dehydrogenase E1 alpha 1 (Pdha1)
GGGACGTCTGTTGAGAGAGC (SEQ ID NO: 57)
TGTGTCCATGGTAGCGGTAA (SEQ ID NO: 58)
NM_008810

Pyruvate dehydrogenase kinase, isoenzyme 4 (Pdk4)
GCTTGCCAATTTCTCGTCTC (SEQ ID NO: 59)
CTTCTCCTTCGCCAGGTTCT (SEQ ID NO: 60)
NM_013743

Ribosomal protein S16 (Rps16)
TGCTGGTGTGGATATTCGGG (SEQ ID NO: 61)
CCTTGAGATGGGCTTATCGG (SEQ ID NO: 62)
XM_003085753.1

Glyceraldehyde-3-phosphate dehydrogenase (Gapdh)
AACGACCCCTTCATTGAC (SEQ ID NO: 63)
TCCACGACATACTCAGCAC (SEQ ID NO: 64)
NM_008084.2

TNF receptor superfamily member 6 (Fas)
CGATTCTCCTGGCTGTGAAC (SEQ ID NO: 65)
TGGAATTAACAAAACAAGGATGG (SEQ ID NO: 66)
NM_007987

Laminin, alpha 1 (Lama1)
ACCAAGGACTTCCTATCCAT (SEQ ID NO: 67)
AGGCGATTTTATACCAGGTT (SEQ ID NO: 68)
NM_008480.2

Transcription factor A, mitochondrial (Tfam)
CAAAAAGACCTCGTTCAGCA (SEQ ID NO: 69)
CTTCAGCCATCTGCTCTTCC (SEQ ID NO: 70)
NM_009360

Ubiquinol-cytochrome c reductase core protein 1 (Uqcrc1)
TGCCAGAGTTTCCAGACCTT (SEQ ID NO: 71)
CCAAATGAGACACCAAAGCA (SEQ ID NO: 72)
NM_025407

Uncoupling protein 2 (Ucp2)
TCTCCTGAAAGCCAACCTCA (SEQ ID NO: 73)
CTACGTTCCAGGATCCCAAG (SEQ ID NO: 74)
NM_011671.4
```

Evaluation of Insulin-Stimulated Akt Phosphorylation

Mice were anesthetized (single intraperitoneal injection of 400 mg chloral hydrate/kg body weight) after a six-hour fast starting at 6 am and mice were injected with 0.01 Unit insulin or saline via the inferior vena cava. Hearts were rapidly excised 5 post minutes post injection, snap frozen in liquid nitrogen, and processed for Western Blot analysis.

Western Blot Analysis

Total protein extraction was performed as previously reported. Proteins were resolved by SDSPAGE and electro-transferred to nitrocellulose (IRS, P/total mTOR, and P/total Acetyl-CoA Carboxylase) or PVDF membranes (other targets). Primary antibodies against 4E-BP1 were purchased from Abcam, Cambridge, Mass.; IRS1 and IRS2 from Millipore, Billerica, Mass.; LC3 and α-Tubulin from Sigma Aldrich, St. Louis, Mo.; Cathepsin D, p62 (SQSTM1), FoxO3 (FKHRL1) and Ulk1 from Santa Cruz Biotechnology; Acetyl-CoA Carboxylase, Akt, AMPKα, Atg7, Beclin1, Bcl-2, Caspase-12, Cleaved PARP (Asp214), FoxO1, GAPDH, mTOR, P-Acetyl-CoA Carboxylase (Ser79), P-Akt (Ser473), P-Akt (Thr308), P-AMPKα (Thr172), P-FoxO1 (Thr24)/FoxO3a (Thr32), P-FoxO3a (Ser318/321), P-mTOR (Ser2448), P-S6 Ribosomal Protein (Ser235/236), P-ULK1 (Ser555), P-ULK1 (Ser757), and S6 Ribosomal Protein from Cell Signaling, Danvers, Mass. Protein detection was carried out with the appropriate horseradish peroxidase-conjugated secondary antibody/ECL detection systems (Amersham Biosciences, Piscataway, N.J.) or Alexa fluor anti-Rabbit 680 (Invitrogen, Carlsbad Calif.) and anti-Mouse 800 (VWR International, West Chester, Pa.) as secondary antibodies and fluorescence quantified using the LI-COR Odyssey imager (Lincoln, Nebr.).

Electron Microscopy

Left ventricular samples were prepared as previously described in the art. Mitochondrial number and volume density were determined by stereology in a blinded fashion using the point counting method as previously described in the art.

Fluorescence Determination of Autophagosomes

Autophagosomes were isolated from tissue samples and incubated with the fluorescent cadaverine compound. Fluorescence was read on a plate reader and adjusted by protein concentration of the sample.

Histology and Stereology

Myocardial fragments were stained with Hematoxylin/Eosin (Fisher, Pittsburgh, Pa.), Masson's trichrome (Sigma-Aldrich), TUNEL (Roche, Indianapolis, Ind.,) or DAPI (Invitrogen, Carlsbad Calif.). Myocardium was analyzed with a 36 point test-system and stereology was performed as previously described in the art.

Measurement of Serum Amino Acids Levels

Serum amino acids levels were determined using gas chromatography-mass spectrometry (GC-MS). Extraction was performed as previously described in the art to remove proteins by precipitation. Briefly, 360 µL of −20° C. 90% methanol (aq.) was added to 40 µL of the individual tubes containing serum to give a final concentration of 80% methanol. The samples were incubated for one hour at −20° C. followed by centrifugation at 30,000×g for 10 minutes using a rotor chilled to −20° C. The supernatant containing the extracted amino acids was then transferred to fresh disposable tubes and completely dried en vacuo. GC-MS analysis was performed with a Waters GCT Premier mass spectrometer fitted with an Agilent 6890 gas chromatograph and a Gerstel MPS2 autosampler. Dried samples were suspended in 40 µL of 40 mg/mL O-methoxylamine hydrochloride (MOX) in pyridine and incubated for one hour at 30° C. This solution (25 µL) was added to autosampler vials, then N-methyl-N-trimethylsilyltrifluoracetamide (MSTFA) was added using the autosampler and incubated for 30 minutes at 37° C. with shaking. The sample (1 µL) was injected to the gas chromatograph inlet in the split mode at a 10:1 split ratio with the inlet temperature held at 250° C. The gas chromatograph had an initial temperature of 95° C. for one minute followed by a 40° C./min ramp to 110° C. and a hold time of 2 minutes. This was followed by a second 5° C./min ramp to 250° C., a third ramp to 350° C., then a final hold time of 3 minutes. A 30 m Phenomenex-ZB5MSi column with a 5 m long guard column was employed for chromatographic separation. Data was collected using MassLynx 4.1 software (Waters). For the targeted approach, known amino acids were identified and their peak area was recorded using QuanLynx.

Preparation of BCAA/Arg Formulation

L-Ile (0.45 g) and L-Leu (0.90 g) were dissolved in 3 ml 1M HCl. Double distilled water (60 ml) was added and the solution stirred until the amino acids were dissolved. L-Val (0.54 g) and L-Arg (0.453 g) were then added and the solution stirred until completely dissolved. Double distilled water was added to a final volume of 75 ml. NaOH (5M) was added until the pH reached about 7.4 (about 20 µl). The solution was filtered (0.22 µm filter, PVDF membrane) prior to use. Amino acids were purchased from Sigma Aldrich, St. Louis, Mo. This formulation is a single embodiment of the disclosure and is not intended to limit the scope of the claimed formulation.

Glucose Tolerance Tests and Insulin Tolerance Tests (ITT)

For glucose tolerance tests, mice were fasted for 6 h fast starting at 6 am and were injected intraperitoneally with 1 g glucose/kg body weight. Insulin tolerance tests were performed on random fed animals by intraperitoneal injection of 0.75 U insulin/kg body weight. Blood glucose concentrations were measured using a glucometer (Bayer Glucometer Elite).

Extraction of Metabolites and Amino Acids for Gas Chromatography-Mass Spectrometry (GC-MS) and Liquid Chromatography-Mass Spectrometry (LC-MS)

Serum amino acids levels were determined using gas chromatography-mass spectrometry (GC-MS). Extraction was performed as previously described in the art to remove proteins by precipitation. Briefly, 360 µL of −20° C. 90% methanol (aq.) was added to 40 µL of the individual tubes containing serum to give a final concentration of 80% methanol. The samples were incubated for one hour at −20° C. followed by centrifugation at 30,000×g for 10 minutes using a rotor chilled to −20° C. The supernatant containing the extracted amino acids was then transferred to fresh disposable tubes and completely dried en vacuo. For measurement of tissue metabolites and amino acid levels, about 40 mg of heart tissue were placed into a bead mill tube containing 1.4 mm ceramic beads (MoBio Laboratories). Weights were recorded for normalization purposes. Methanol (aq) was added to the tubes that had been chilled to −20° C. to a final concentration of 80% Methanol (aq) and 20% tissue homogenate. Samples were homogenized for 30 seconds at 6.5 m/sec using an Omni Bead Ruptor 24 bead mill (Omni-Inc.) and incubated for one hour at −20° C. to precipitate protein. Following incubation, cell debris was pelleted by centrifugation (14,000 g for 5 min at 4° C.) and the supernatant reserved. A second extraction of the pellet was performed by the addition of −20° C. Methanol (aq) to a final concentration of 50% Methanol (aq) and 50% tissue homogenate. Each sample was mixed by vortex, incubated for one hour at −20° C., and centrifuged (14,000 g for 5 min at 4° C.) to remove cell debris. The two extracts were combined, mixed, and then split in half to new tubes. Samples were dried en vacuo.

Gas Chromatography-Mass Spectrometry (GC-MS) Analysis

GC-MS analysis was performed with a Waters GCT Premier mass spectrometer fitted with an Agilent 6890 gas chromatograph and a Gerstel MPS2 autosampler. Dried samples were suspended in 40 µL of 40 mg/mL Omethoxylamine hydrochloride (MOX) in pyridine and incubated for one hour at 30° C. This solution (25 µL) was added to autosampler vials, then 20 µL of N-methyl-N-trimethylsilyltrifluoracetamide (MSTFA) was added using the autosampler and incubated for 60 minutes at 37° C. with shaking. The sample (1 µL) was injected to the gas chromatograph inlet in the split mode at a 10:1 split ratio with the inlet temperature held at 250° C. The gas chromatograph had an initial temperature of 95° C. for one minute followed by a 40° C./min ramp to 110° C. and a hold time of 2 minutes. This was followed by a second 5° C./min ramp to 250° C., a third ramp to 350° C., then a final hold time of 3 minutes. A 30 m Phenomenex-ZB5MSi column with a 5 m long guard column was employed for chromatographic separation. Data was collected using MassLynx 4.1 software (Waters). A two-step process was employed for data analysis, a targeted followed by non-targeted analysis. For the targeted approach, known metabolites and amino acids were identified and their peak area was recorded using QuanLynx. For the non-targeted approach, peak picking and analysis was performed using MarkerLynx. Principle component analysis (PCA) and partial least squares-discriminate analysis (PLS-DA) was performed using SIMCA-P 12.0 (Umetrics). Potential metabolite biomarkers were further investigated by manually recording the peak area. Metabolite identity was established using a combination of an in house metabolite library developed using pure purchased standards and the commercially available NIST library.

Liquid Chromatography-Mass Spectrometry (LC-MS) Analysis

LC-MS was performed using an Agilent 6520 QTOF-MS fitted with an Agilent 1100 LC. Each sample was suspended in 10 µL of 10 mM ammonium acetate (pH 6.8) and 90 µL of acetonitrile and placed into a chilled auto sampler tray (CTC Analytics). Each sample was analyzed using two separate column chemistries, a SeQuant ZIC-HILIC at pH 3.2 in the positive mode and a SeQuant ZIC-pHILIC at pH 9.2 in the negative mode (Merck KGaA). Samples (3 µL each) were injected into each column with initial conditions set to 90% acetonitrile/10% buffer (10 mM ammonium formate pH 3.2 for HILIC chromatography or 10 mM ammonium formatate pH 9.2 for pHILIC chromatography) for one minute followed by a 20 minute ramp to 40% acetonitrile/60% buffer. The flow rate was set to 0.2 mL/min. Detection was performed in the positive mode for the HILIC analysis and the negative mode for the pHILIC analysis. Data analysis was performed using Mass Hunter Qual and Mass Profiler Professional (Agilent).

Various embodiments are described herein which may be useful independently, in combinations thereof, and as a whole. The following experimental results demonstrate that loss of IRS signaling prevents the physiological suppression of autophagy that parallels the postnatal increase in circulating insulin, glucose and amino acid concentrations. This resulted in unrestrained autophagy in cardiomyocytes leading to myocyte loss, heart failure and premature death. This process may be ameliorated by pharmacological and genetic suppression of autophagic activation. It is through this mechanism that the BCAA/Arg formulation may treat heart disease and other disease indications in which autophagy participates in the pathological mechanism.

Experimental Results

To test the hypothesis that insulin suppresses postnatal autophagy in the heart, insulin and IGF-1R signaling was disrupted in mice by combined cardiomyocyte-specific deletion of IRS1 and IRS2 (CIRS12KO). Cardiomyocyte-specific deletion of both IRS1 and IRS2 proteins was confirmed by immunoblotting in 4-week-old mice (FIG. 1A). The CIRS12KO hearts developed dilated cardiomyopathy (FIG. 1B) and showed increased expression of hypertrophy markers (FIG. 1C). Basal levels of Akt phosphorylation (Ser473) in CIRS12KO hearts were similar to wild type (WT) controls in 4-week-old mice. Insulin (0.01 U) was then injected into the inferior vena cava of the mice. In contrast to the similar basal levels, insulin-stimulated Akt phosphorylation was impaired by 71.6% in CIRS12KO mice compared to WT controls ($p<0.05$) (FIG. 1D). Histology revealed age-dependent myofibrillar loss and disarray, and increased fibrosis (FIGS. 1E-1H). To determine when loss of IRS1 and IRS2 induced cardiac dysfunction, CIRS12KO hearts were examined immediately after birth. Both IRS isoforms were absent in CIRS12KO hearts isolated from these 1-day-old mice. However, light microscopy revealed normal gross cardiac histology and no increase in fibrotic tissue at one day of age and cardiac function was preserved. Phosphorylation of insulin-activated targets such as Akt (Ser473), S6 (Ser235/236), and mTOR (Ser2448) was reduced by 44.7% to 85.1% respectively ($p<0.05$) (FIG. 1I). Levels of the γ-band of 4E-BP1 (corresponding to phosphorylated moiety) were reduced by 51% (FIG. 1I), raising the possibility that global protein synthesis could be impaired in CIRS12KO hearts.

A cohort of CIRS12KO mice and WT littermate controls were monitored starting from birth. All CIRS12KO died by the age of eleven weeks with the majority dying by eight weeks of life (FIG. 1J). Transthoracic echocardiography revealed age-dependent impairment of contractile function and left ventricular dilation (FIGS. 1K-L and Tables 2 and 3).

TABLE 2

Cardiac function of CIRS12KO mice

| Group (n) | Age | LVDd [mm] | LVDs [mm] | IVSDd [mm] |
|---|---|---|---|---|
| WT (15) | 1 d | 1.34 ± 0.03 | 0.73 ± 0.03 | n.d. |
| CIRS12KO (12) | 1 d | 1.40 ± 0.03 | 0.78 ± 0.04 | |
| WT (10) | 2 wk | 2.55 ± 0.07 | 1.78 ± 0.08 | n.d. |
| CIRS12KO (6) | 2 wk | 2.46 ± 0.11 | 1.77 ± 0.13 | |
| WT, Male (4) | 4 wk | 3.44 ± 0.18 | 2.38 ± 0.13 | 0.56 ± 0.03 |
| CIRS12KO, Male (5) | 4 wk | 3.58 ± 0.15 | 2.97 ± 0.18* | 0.43 ± 0.03* |
| WT, Female (12) | 4 wk | 3.40 ± 0.09 | 2.46 ± 0.09 | 0.53 ± 0.01 |
| CIRS12KO, Female (10) | 4 wk | 3.48 ± 0.07 | 2.87 ± 0.12* | 0.42 ± 0.02* |

| Group (n) | IVSDs [mm] | LVPWd [mm] | LVPWs [mm] | FS [%] | EF [%] |
|---|---|---|---|---|---|
| WT (15) | n.d. | 0.39 ± 0.02 | 0.56 ± 0.02 | 45.35 ± 2.10 | 82.6 ± 2.1 |
| CIRS12KO (12) | | 0.31 ± 0.02* | 0.51 ± 0.02 | 44.29 ± 2.39 | 81.7 ± 2.1 |
| WT (10) | n.d. | 0.49 ± 0.03 | 0.65 ± 0.04 | 30.34 ± 1.86 | 65.6 ± 2.6 |
| CIRS12KO (6) | | 0.41 ± 0.02* | 0.57 ± 0.06 | 28.39 ± 3.16 | 62.2 ± 4.3 |
| WT, Male (4) | 0.98 ± 0.04 | 0.58 ± 0.01 | 0.89 ± 0.03 | 30.65 ± 0.16 | 66.7 ± 0.2 |
| CIRS12KO, Male (5) | 0.63 ± 0.05* | 0.52 ± 0.01* | 0.69 ± 0.03* | 17.22 ± 2.63* | 42.6 ± 5.5* |
| WT, Female (12) | 0.85 ± 0.03 | 0.53 ± 0.01 | 0.82 ± 0.03 | 27.80 ± 1.23 | 57.5 ± 5.0 |

TABLE 2-continued

Cardiac function of CIRS12KO mice

| | | | | | |
|---|---|---|---|---|---|
| CIRS12KO, Female (10) | 0.61 ± 0.03* | 0.46 ± 0.02* | 0.65 ± 0.03* | 18.47 ± 2.04* | 44.9 ± 4.1 (p = 0.067 vs. WT Female same age) |

Data are reported as mean values ± SEM.
*p <0.05 vs. WT same age (unpaired Student's t-test)
n.d., not determined;
LVDd, Left ventricular cavity diameter at diastole;
LVDs, Left ventricular cavity diameter at systole;
IVSDd, Interventricular septum diameter at diastole;
IVSDs, Interventricular septum diameter at systole;
LVPWd, Left ventricular posterior wall thickness at diastole;
LVPWs, Left ventricular posterior wall thickness at systole;
FS, Fractional shortening;
EF, Ejection fraction.

TABLE 3

Heart weights of CIRS12KO mice

| Group (n) | Age | BW [g] | HW [mg] |
|---|---|---|---|
| WT (15) | 1 d | 1.23 ± 0.05 | 7.6 ± 0.4 |
| CIRS12KO (15) | 1 d | 1.26 ± 0.06 | 7.2 ± 0.4 |
| WT (8) | 2 wk | 6.67 ± 0.38 | 40.9 ± 2.1 |
| CIRS12KO (8) | 2 wk | 6.46 ± 0.45 | 30.8 ± 1.5* |
| WT, Male (10) | 4 wk | 14.89 ± 0.41 | 69.8 ± 2.4 |
| CIRS12KOMale (10) | 4 wk | 12.79 ± 0.92 | 66.4 ± 4.7 |
| WT, Female (10) | 4 wk | 13.19 ± 0.57 | 67.2 ± 2.3 |
| CIRS12KO, Female (10) | 4 wk | 11.69 ± 0.58 | 68.9 ± 6.5 |

| Group (n) | TL [mm] | HW/BW [mg/g] | HW/TL [mg/mm] |
|---|---|---|---|
| WT (15) | n.d. | 6.16 ± 0.20 | n.d. |
| CIRS12KO (15) | | 5.80 ± 0.26 | |
| WT (8) | n.d. | 6.16 ± 0.21 | n.d. |
| CIRS12KO (8) | | 4.85 ± 0.21* | |
| WT, Male (10) | 13.53 ± 0.20 | 4.70 ± 0.13 | 5.16 ± 0.16 |
| CIRS12KOMale (10) | 13.38 ± 0.45 | 5.53 ± 0.77 | 5.05 ± 0.50 |
| WT, Female (10) | 13.20 ± 0.34 | 5.15 ± 0.20 | 5.13 ± 0.24 |
| CIRS12KO, Female (10) | 12.63 ± 0.35 | 6.13 ± 0.84 | 5.51 ± 0.58 |

Data are reported as mean values ± SEM.
*p <0.05 vs. WT same age (unpaired Student's t-test)
BW, Body weight;
HW, Heart weight;
TL, Tibia length;
n.d.; not determined.

Transcriptional analysis in hearts of one-day-old CIRS12KO mice showed preserved expression of genes involved in fatty acid oxidation (FAO), oxidative phosphorylation (OXPHOS), and their transcriptional regulators PGC-1α (Ppargc1a) and PGC-1β (Ppargc1b). However, at four weeks of age when contractile function was markedly impaired, FAO and OXPHOS gene expression was repressed by 27.6 to 61.5%, in concert with repressed PGC-1α and PGC-1β expression (47.5%, 32.7% respectively, p<0.05) (FIG. 1M). Specifically, FIG. 1M illustrates age-dependent repression of mRNAs encoding genes involved in fatty acid and glucose oxidation, oxidative phosphorylation and their transcriptional regulators in CIRS12KO hearts (n=6-8, Cphn was used for normalization for 1 day and 4 week old mice, Lama1 for 2 week old mice respectively). Data for mRNA expression are presented as fold change compared to WT same age (=1.0). Gene names are shown in Table 1. Furthermore, analysis of the mitochondrial proteome revealed reduced content of proteins involved in the tricarboxylic acid (TCA) cycle and in fatty acid metabolism (Tables 4-5).

TABLE 4

Summary of changes in mitochondrial protein abundance in mitochondria obtained from 4 week old CIRS12KO hearts compared age matched WT controls (IRS1lox/lox:IRS2lox/lox)

| | Decreased | Increased | Total Detected |
|---|---|---|---|
| Citrate Cycle (matrix fraction) | 5 | 2 | 10 |
| Fatty Acid Oxidation (membrane fraction) | 6 | 0 | 15 |
| Oxidative Phosphorylation (membrane fraction | 2 | 5 | 42 |

TABLE 5

Mitochondrial abundance of proteins involved in citrate cycle, pyruvate decarboxylation, fatty acid oxidation, and oxidative phosphorylation in CIRS12KO hearts (4 wk), presented as fold change compared to age matched WT hearts (IRS1lox/lox:IRS2lox/lox). Footnoted (* and †) cells indicate a significant difference compared to WT (* = increased, † = decreased).

| Canonical Pathway | Accession | CIRS12KO |
|---|---|---|
| Citrate cycle (matrix fraction) | | |
| aconitase 2, mitochondrial | NP 542364.1 | 0.88† |
| citrate synthese | NP 080720.1 | 0.92† |
| dihydrolipoamide dehydrogenase | NP 031887.2 | 0.94 |
| dihydrolipoamide 5-succinyltransferase (E2 component of 2-oxo-glutarate complex) | NP 084501.1 | 1.09 |

TABLE 5-continued

Mitochondrial abundance of proteins involved in citrate cycle, pyruvate decarboxylation, fatty acid oxidation, and oxidative phosphorylation in CIRS12KO hearts (4 wk), presented as fold change compared to age matched WT hearts (IRS1lox/lox:IRS2lox/lox). Footnoted (* and †) cells indicate a significant difference compared to WT (* = increased, † = decreased).

| Canonical Pathway | Accession | CIRS12KO |
|---|---|---|
| fumarate hydratase 1 | NP 034339.1 | 1.01 |
| isocitrate dehydrogenase 2 (NADP+), mitochondrial | NP 766599.1 | 0.93† |
| isocitrate dehydrogenase 3 (NAD+) alpha | NP 083849.1 | 0.88† |
| malate dehydrogenase 2, NAD (mitochondrial) | NP 032643.2 | 1.10* |
| oxoglutarate dehydrogenase (lipoamide) | NP 035086.2 | 1.11* |
| succinate-Coenzyme A ligase, ADP-forming, beta subunit | NP 035636.1 | 0.88† |
| Pyruvate decarboxylation (matrix fraction) | | |
| | | |
| pyruvate dehydrogenase (lipoamide) beta | NP 077183.1 | 0.99 |
| pyruvate dehydrogenase E1 alpha 1 | NP 032836.1 | 0.95 |
| Fatty acid oxidation (membrane-fraction) | | |
| | | |
| acetyl-Coenzyme A acetyltransferase 1 precursor | NP 659033.1 | 0.84 |
| acetyl-Coenzyme A acyltransferase 2 (mitochondrial 3-oxoacyl-Coenzyme A thiolase) | NP 803421.1 | 0.76† |
| acetyl-Coenzyme A dehydrogenase, long-chain | NP 031407.2 | 1.03 |
| acetyl-Coenzyme A dehydrogenase, medium chain | NP 031408.1 | 0.76† |
| acyl-CoA synthetase long-chain family member 1 | NP 032007.2 | 0.93 |
| acyl-Coenzyme A dehydrogenase, very long chain | NP 059062.1 | 0.93 |
| carnitine palmitoyltransferase 1b, muscle | NP 034078.1 | 1.04 |
| carnitine palmitoyltransferase 2 | NP 034079.1 | 0.80† |
| hydroxyacyl-Coenzyme A dehydrogenase/3-ketoacyl-Coenzyme A thiolase/enoyl- Coenzyme A hydratase (trifunctional protein), alpha subunit | NP 849209.1 | 0.82† |
| hydroxyacyl-Coenzyme A dehydrogenase/3-ketoacyl-Coenzyme A thiolase/enoyl- Coenzyme A hydratase (trifunctional protein), beta subunit | NP 663513.1 | 0.83† |
| L-3-hydroxyacyl-Coenzyme A dehydrogenase, short chain | NP 032238.1 | 0.55† |
| PREDICTED: similar to acyl-CoA synthetase long-chain family member 1 isoform 2 | XP 996295.1 | 0.90 |
| PREDICTED: similar to acyl-CoA synthetase long-chain family member 1 isoform 3 | XP 996322.1 | 0.88 |
| PREDICTED: similar to acyl-CoA synthetase long-chain family member 1 isoform 4 | XP 996347.1 | 0.92 |
| PREDICTED: similar to acyl-CoA synthetase long-chain family member 1 isoform 5 | XP 996374.1 | 0.93 |
| Oxidative phosphorylation (membrane fraction) Complex I | | |
| | | |
| NADH dehydrogenase (ubiquinone) 1 alpha subcomplex 10 | NP 077159.1 | 1.02 |
| NADH dehydrogenase (ubiquinone) 1 alpha subcomplex, 13 | NP 075801.1 | 1.10 |
| NADH dehydrogenase (ubiquinone) 1 alpha subcomplex, 2 | NP 035015.2 | 1.16 |
| NADH dehydrogenase (ubiquinone) 1 alpha subcomplex, 4 | NP 035016.1 | 1.39* |
| NADH dehydrogenase (ubiquinone) 1 alpha subcomplex, 9 | NP 079634.1 | 0.94 |
| NADH dehydrogenase (ubiquinone) 1 beta subcomplex 8 | NP 080337.1 | 1.12 |
| NADH dehydrogenase (ubiquinone) 1 beta subcomplex, 10 | NP 080960.1 | 1.14 |
| NADH dehydrogenase (ubiquinone) 1, subcomplex unknown, 2 | NP 077182.1 | 1.06 |
| NADH dehydrogenase (ubiquinone) Fe—S protein 1 | NP 663493.1 | 1.05 |
| NADH dehydrogenase (ubiquinone) Fe—S protein 2 | NP 694704.1 | 1.16* |
| NADH dehydrogenase (ubiquinone) Fe—S protein 3 | NP 080964.1 | 0.98 |
| NADH dehydrogenase (ubiquinone) Fe—S protein 5 | NP 001025445.1 | 1.14 |
| NADH dehydrogenase (ubiquinone) Fe—S protein 6 | NP 035018.1 | 1.04 |
| NADH dehydrogenase (ubiquinone) Fe—S protein 8 | NP 659119.2 | 1.16 |
| NADH dehydrogenase (ubiquinone) flavoprotein 1 | NP 598427.1 | 1.12* |
| Complex II | | |
| | | |
| succinate dehydrogenase Fp subunit | NP 075770.1 | 0.97 |
| succinate dehydrogenase Ip subunit | NP 075863.2 | 0.99 |
| Complex III | | |
| | | |
| ubiquinol cytochrome c reductase core protein 2 | NP 080175.1 | 0.97 |
| ubiquinol-cytochrome c reductase binding protein | NP 080495.1 | 1.04 |
| ubiquinol-cytochrome c reductase core protein 1 | NP 079683.2 | 1.00 |
| ubiquinol-cytochrome c reductase hinge protein | NP 079917.1 | 0.95 |
| ubiquinol-cytochrome c reductase, Rieske iron-sulfur polypeptide 1 | NP 079986.1 | 1.16* |
| neuronal protein 15.6 | NP 062308.1 | 1.16 |
| Complex IV | | |
| | | |
| cytochrome c oxidase subunit II | NP 904331.1 | 0.97 |
| cytochrome c oxidase subunit IV isoform 1 | NP 034071.1 | 0.87† |

TABLE 5-continued

Mitochondrial abundance of proteins involved in citrate cycle, pyruvate decarboxylation, fatty acid oxidation, and oxidative phosphorylation in CIRS12KO hearts (4 wk), presented as fold change compared to age matched WT hearts (IRS1lox/lox:IRS2lox/lox). Footnoted (* and †) cells indicate a significant difference compared to WT (* = increased, † = decreased).

| Canonical Pathway | Accession | CIRS12KO |
|---|---|---|
| cytochrome c oxidase, subunit Va | NP 031773.1 | 1.09 |
| cytochrome c oxidase, subunit VIb polypeptide 1 | NP 079904.1 | 0.92 |
| cytochrome c oxidase, subunit VIc | NP 444301.1 | 0.90 |
| cytochrome c oxidase, subunit VIIa 1 | NP 034074.1 | 5.56* |
| cytochrome c oxidase, subunit VIIa 2 | NP 034075.2 | 1.11 |
| Complex V | | |
| ATP synthase, H+ transporting mitochondrial F1 complex, beta subunit | NP 058054.2 | 1.00 |
| ATP synthase, I—I+ transporting, mitochondrial F0 complex, subunit b, isoform 1 | NP 033855.2 | 1.06 |
| ATP synthase, H+ transporting, mitochondrial F0 complex, subunit d | NP 082138.1 | 0.99 |
| ATP synthase, H+ transporting, mitochondrial F0 complex, subunit F | NP 058035.1 | 0.93 |
| ATP synthase, H+ transporting, mitochondrial F0 complex, subunit f, isoform 2 | NP 065607.1 | 0.92 |
| ATP synthase, I—I+ transporting, mitochondrial F1 complex, alpha subunit, isoform 1 | NP 031531.1 | 0.92† |
| ATP synthase, H+ transporting, mitochondrial F1 complex, delta subunit precursor | NP 079589.1 | 1.14 |
| ATP synthase, I—I+ transporting, mitochondrial F1 complex, gamma subunit | NP 065640.1 | 1.08 |
| ATP synthase, I—I+ transporting, mitochondrial F1 complex, 0 subunit | NP 613063.1 | 1.05 |
| Other | | |
| cytochrome c-1 | NP 079843.1 | 1.16 |
| hypothetical protein LOC66152 | NP 932096.1 | 1.08 |
| low molecular mass ubiquinone-binding protein | NP 079628.1 | 0.98 |

Expression of genes involved in OXPHOS and FAO was decreased by up to 50% at two weeks of age, at a time when cardiac contractile function was preserved. Saponin-permeabilized cardiac fibers were then used to assess mitochondrial function. Fibers obtained from CIRS12KO hearts revealed impaired succinate-supported ADP-stimulated mitochondrial oxygen consumption (VADP) and ATP production at two weeks of age (−36.2%, −35.1% respectively, $p<0.05$ each) (FIGS. 1N and 1O). Similarly, VADP and ATP synthesis were decreased by 32.7 to 41.1% at four weeks of age ($p<0.05$) using Pyruvate, Palmitoyl-Carnitine or Glutamate as substrates ($p<0.05$) (FIGS. 1Q and 1R). ATP/O ratios were not changed at either time point suggesting preserved mitochondrial coupling (FIGS. 1P and 1S). Thus mitochondrial dysfunction clearly precedes the onset of contractile dysfunction and may contribute to heart failure in CIRS12KO mice.

Figure 2B:
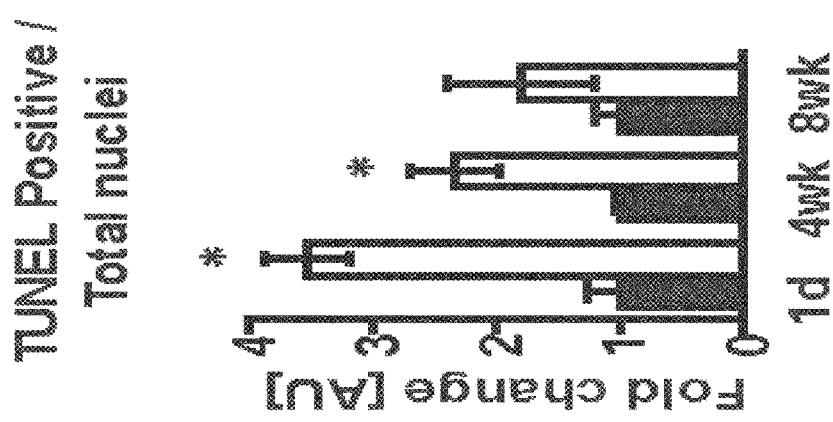
FIG. 2B is a graphical representation of autophagy quantified by cadaverine fluorescence staining of autophagosomes.
Figure 2A:
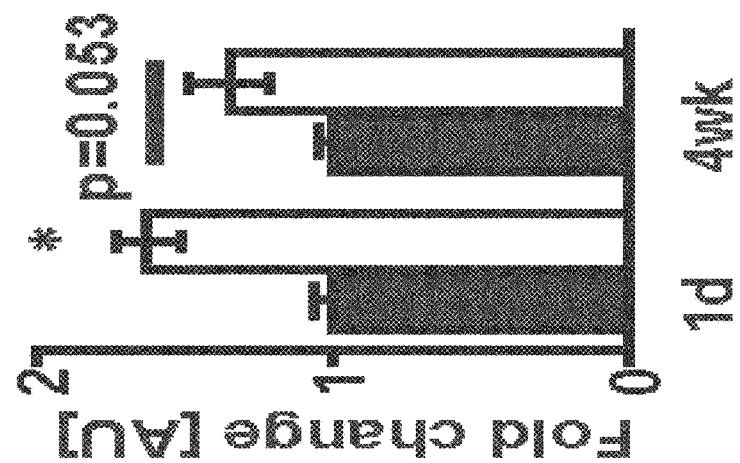
FIG. 2A is a graphical representation of representative stereological quantification of TUNEL and DAPI stains.
Figure 2C:
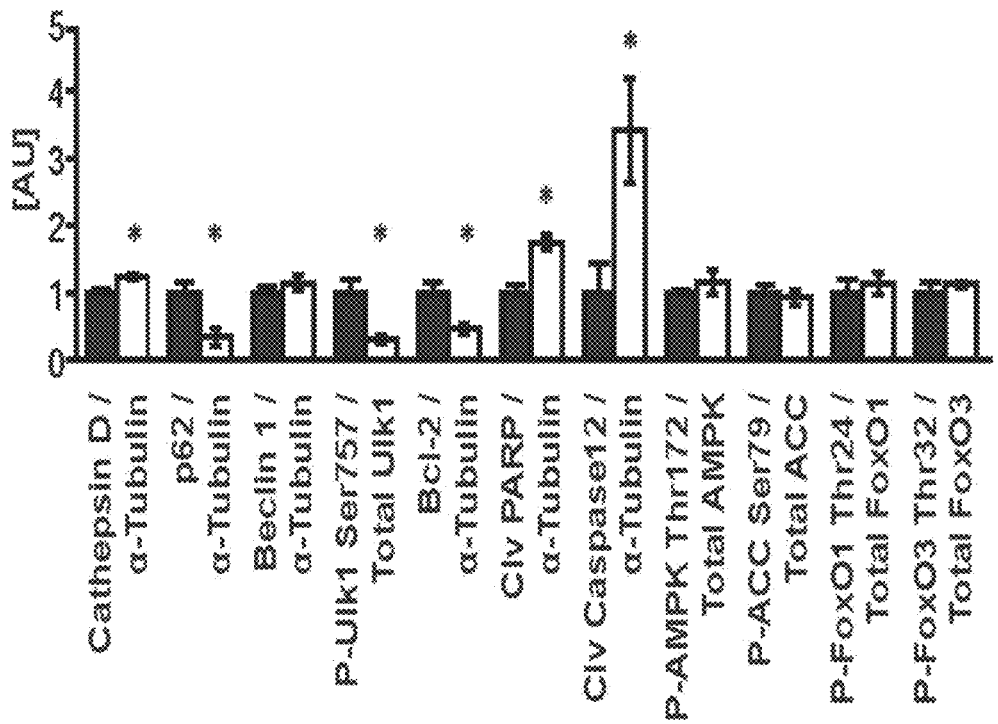
FIG. 2C is a graphical representation of densitometric quantification of immunoblots stained for proteins involved in autophagy regulation and cell survival (n=3-6).
Figure 2D:
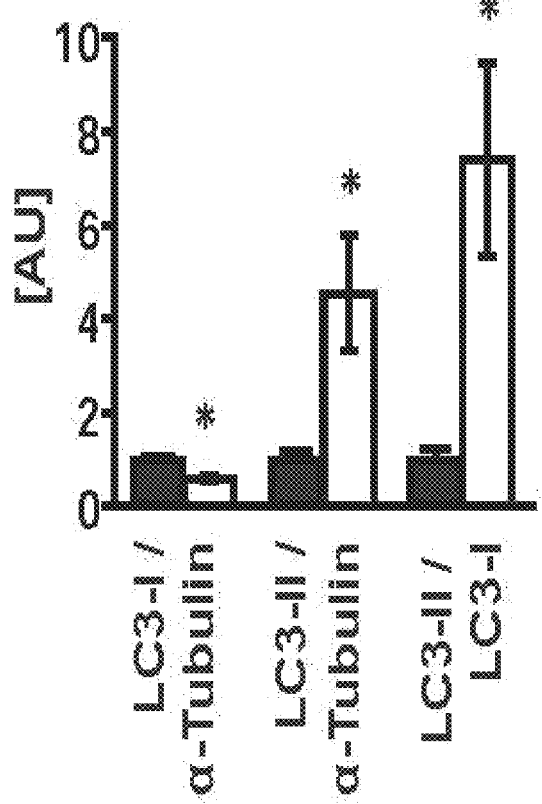
FIG. 2D is a graphical representation of LC3-II to LC3-I expression as assessed by immunoblotting.
Figure 2E:
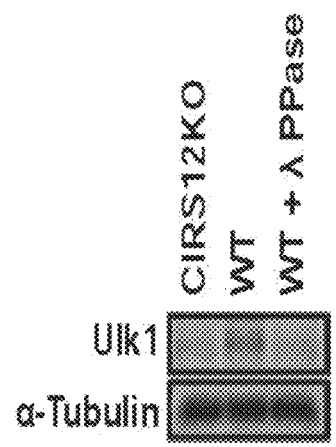
FIG. 2E shows an immunoblot stained for Ulk1.

Apoptosis, estimated by the ratio of TUNEL positive to total nuclei, was maximally increased in 1-day-old CIRS12KO hearts (FIG. 2A, white bars) relative to hearts in wild type mice (FIG. 2A, black bars), but declined as animals aged. Autophagosome content quantified by cadaverine fluorescence was increased by 63% in CIRS12KO at 1 day of age ($p<0.05$) and remained increased by 35% ($p=0.053$) at the age of four weeks (FIG. 2B). This was supported by evidence of increased numbers of autophagic vesicles seen in electron micrographs prepared from 1-day-old CIRS12KO hearts (FIG. 2B). The graph shown in FIG. 2B illustrates that autophagy was increased in CIRS12KO mice (white bars) relative to WT (black bars) by 63% at the age of 1D and by 35% at the age of four weeks ($p=0.053$), n=6. In addition, expression of the pro-apoptotic proteins, Cleaved PARP and Cleaved Caspase 12, was increased whereas expression of the antiapoptotic protein, Bcl-2, was decreased consistent with increased apoptotic cell death signaling. LC3-II/LC3-I ratio, an indicator of autophagy, was assessed by immunoblotting and found to be increased 7.4-fold at 1 day of age (FIG. 2D). This was paralleled by increased protein levels of Cathepsin D (+23%), and reduced levels of p62 (−54%) providing additional evidence for increased autophagy in CIRS12KO hearts (FIG. 2C). Ulk1 phosphorylation at the mTOR dependent Ser757 site was reduced in CIRS12KO hearts (FIG. 2C). The latter biochemical evidence has been suggested to mediate mTOR dependent repression of autophagy induction. As seen in the blot presented in FIG. 2E, knockdown of IRS1 and IRS2 resulted in a mobility shift of Ulk1, which was also observed following phosphatase treatment of wild type control. This suggests impaired Ulk1 phosphorylation in CIRS12KO hearts. Interestingly, phosphorylation of FoxO1 (Thr24) and FoxO3 (Thr32) was preserved and no differences in the phosphorylation of AMPK (Thr172) and the AMPK downstream target Acetyl-CoA Carboxylase (ACC, Ser79) were observed (FIG. 2C). Moreover, expression of genes involved in autophagy regulation and cell death was largely unchanged. Thus, without being limited to any one theory, regulatory mechanisms downstream of mTOR may account for the increase in autophagy and progressive cell loss in CIRS12KO hearts.

Figure 2F:
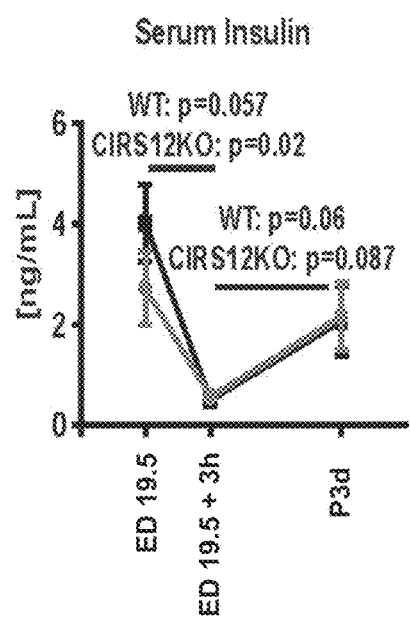
FIG. 2F is a graphical representation of a time course of serum insulin in wild type and CIRS12KO mice in the first three days of life.
Figure 2G:
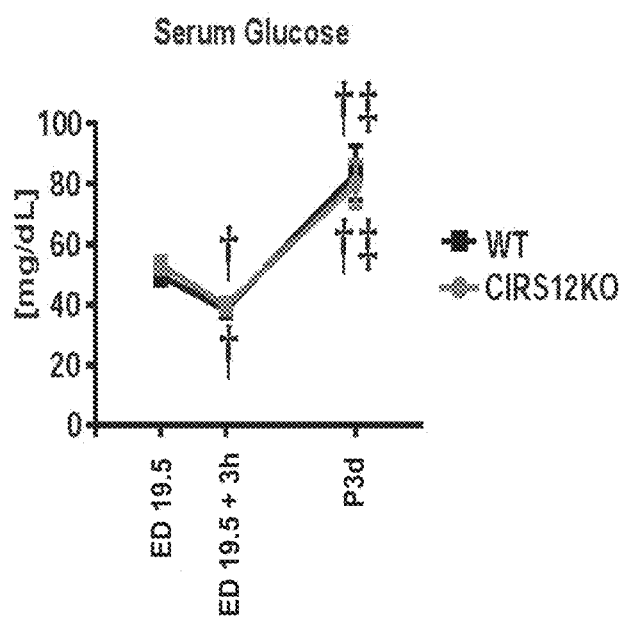
FIG. 2G is graphical representation of a time course of serum glucose in wild type and CIRS12KO mice in the first three days of life.
Figure 2H:
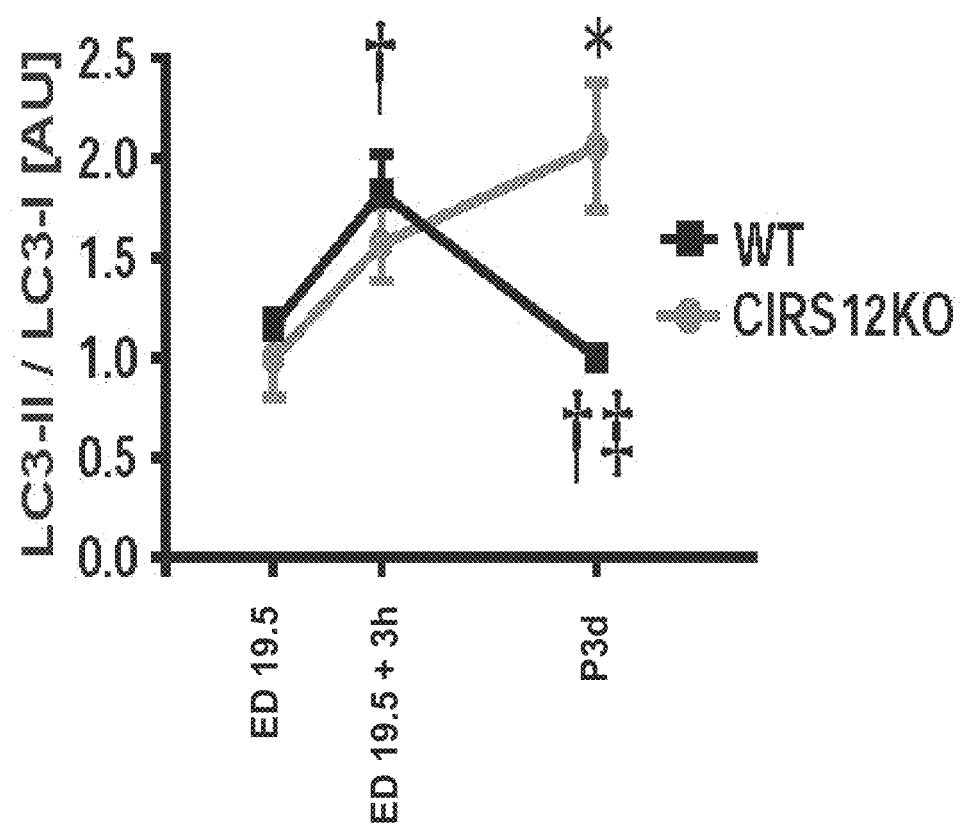
FIG. 2H is a graphical representation of a time course of autophagy as assessed by LC3-II/LC3-I immunoblotting in wild type and CIRS12KO mouse hearts in the first three days of life.
Figure 2I:
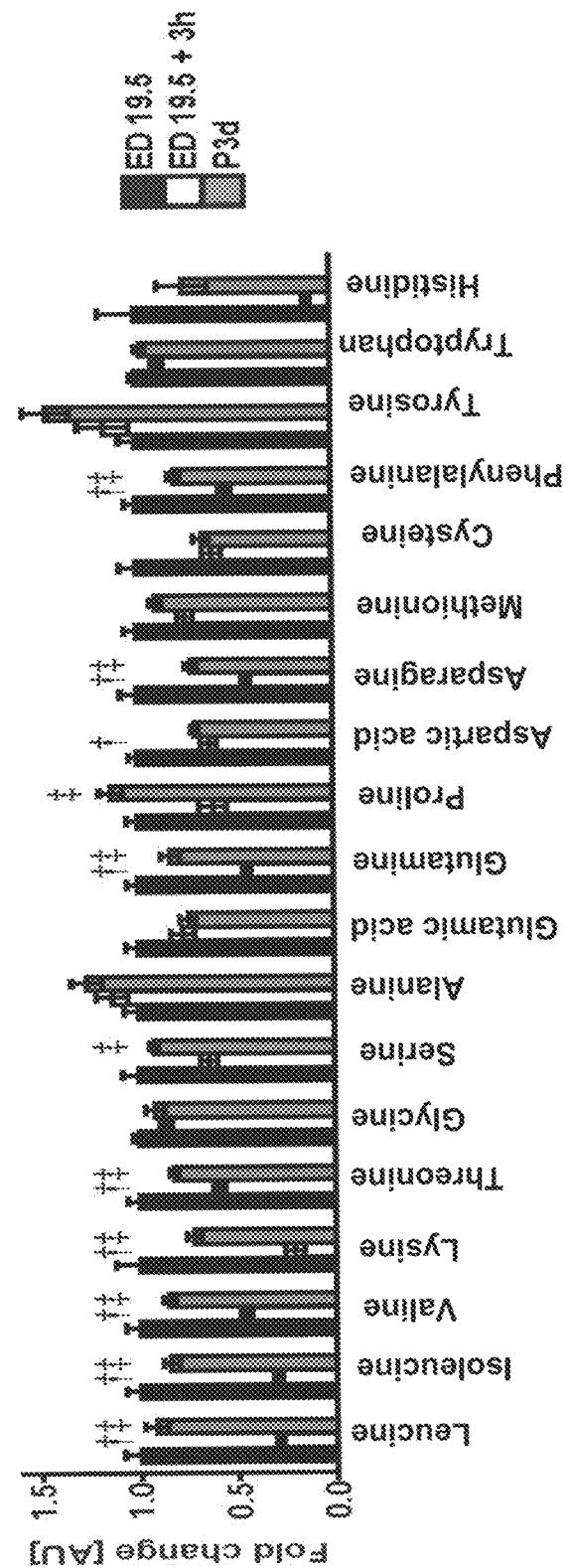
FIG. 2I is a graph illustrating serum amino acid levels in wild type mice at the indicated time points in the first three days of life.

To understand potential mechanisms that may induce neonatal autophagy and to explore potential mechanisms for autophagy repression following the establishment of feeding, autophagy levels in WT and CIRS12KO mice in the perinatal time period were examined and correlated with changes in circulating concentrations of glucose, insulin and amino acids. Loss of both IRS isoforms was confirmed in CIRS12KO hearts at embryonic day (ED) 19.5. Autophagy levels were low in cardiac tissue obtained from ED 19.5 mice when examined in samples immediately following caesarian (C) section. Three hours after C-section, insulin (FIG. 2F) and amino acid (FIG. 2I) concentrations fell by greater than 75% and glucose concentrations (FIG. 2G) by 30% in mice of all genotypes and increased with feeding at 3 days. Autophagy increased to a similar extent in WT and CIRS12KO hearts 3 h post C-section (FIG. 2H), suggesting that autophagy induction might be independent of falling insulin concentrations.

Although insulin, glucose and amino acid concentrations increased in three-day-old mice, autophagy declined only in WT mice but remained elevated in CIRS12KO mouse hearts (FIGS. 2F-I). Milk was found in the stomachs of all mice sacrificed at three days. CIRS12KO hearts exhibited impaired insulin-mediated signaling both under basal conditions at the age of one day and following insulin stimulation (FIGS. 1D and 1I). Thus, these data would lead one of skill in the art to conclude that IRS signaling mediates the physiological suppression of postnatal autophagy when feeding is established and insulin levels rise, and that rising circulating concentrations of glucose and amino acids are insufficient to suppress perinatal autophagy in the heart in the absence of IRS signaling.

Figures 3H, 3I:
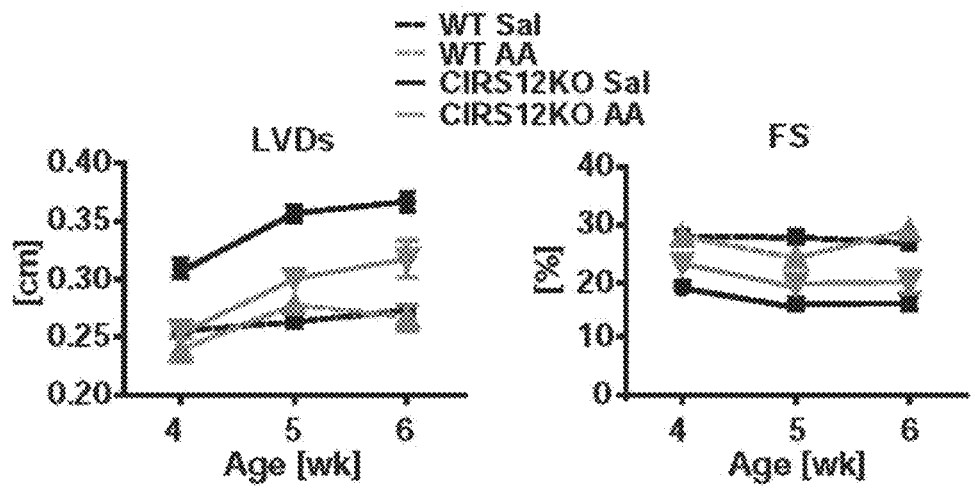
FIG. 3H is a graph illustrating a time course for left ventricular cavity diameter at systole (LVDs) (n=6-9).
FIG. 3I is a graph illustrating a time course for fractional shortening (FS) in mice described in FIG. 3H (n=6-9).
Figures 3J, 3K:
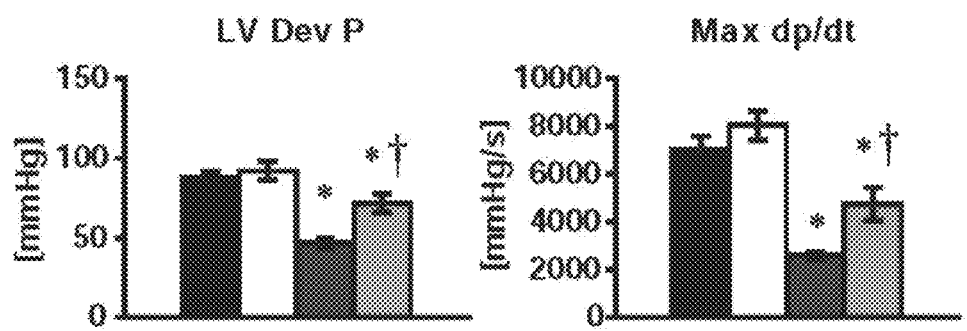
FIG. 3J is a graph illustrating invasive measurement of developed left ventricular pressures at six weeks of age as assessed by catheterization. LV Dev P=left ventricular developed pressure.
FIG. 3K is a graph illustrating maximal rate of increase in left ventricular pressure (Max dp/dt) in mice described in FIG. 3J.
Figures 3L, 3M:
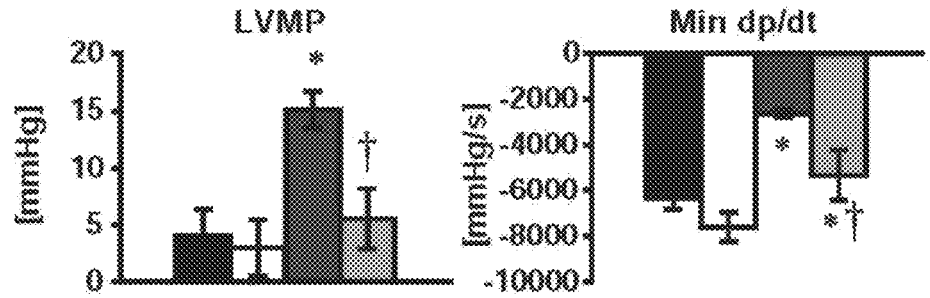
FIG. 3L is a graph illustrating left ventricular minimum pressure (LVMP) in mice described in FIG. 3J.
FIG. 3M is a graph illustrating maximal rate of decrease in left ventricular pressure (Min dp/dt) in mice described in FIG. 3J.

To test the hypothesis that decreased mTOR signaling could account for increased autophagy leading to heart failure, mTOR was hyperactivated with amino acids to determine if this would be sufficient to inhibit autophagy and prevent heart failure. BCAAs and Arginine are powerful activators of mTOR and p70 S6 kinase (S6K1) signaling. Thus, mTOR activity was restored in CIRS12KO hearts to levels of WT controls by daily intraperitoneal administration of a BCAA/Arg solution starting on the day of birth. This time point was chosen because the highest rates of autophagy and cell death were observed that also preceded gross changes in cardiac structure and function. Metabolic analysis confirmed increased BCAA/Arg levels in serum and heart tissue as compared with saline-treated controls (Table 12). BCAA/Arg supplementation attenuated left ventricular dilation (FIG. 3A) and significantly increased the average lifespan of CIRS12KO mice compared to saline treated controls from 6.6 to 11.1 weeks (FIG. 3B). Specifically, the graph of FIG. 3B indicates that BCAA/Arg supplementation increased the average lifespan of CIRS12KO mice from 6.6 to 11.1 weeks (p=0.0001, Log-rank Test). Furthermore, the pathological increase both in heart weights and wet lung weights (pulmonary congestion) was prevented after six weeks of BCAA/Arg treatment (FIGS. 3C, 3D, and Table 6) consistent with reversal of heart failure. Stereological analysis showed reduced cell loss and replacement fibrosis in CIRS12KO hearts following BCAA/Arg treatment relative to saline treated controls (FIGS. 3 E-G). Also, transthoracic echocardiography revealed attenuated left ventricular dilation (LVDs) and partial restoration of contractile function (FIGS. 3H, 3I and Table 7). FIG. 3H shows that mean LVDs in week 4 was significantly lower than week 6 (0.265 cm vs. 0.308 cm, p<0.001). Furthermore, FIG. 3H shows that in week 4, mean LVDs in BCAA/Arg treated CIRS12KO mice (0.256 cm) was lower than saline-treated CIRS12KO mice (0.310 cm, p<0.001), and not significantly different from wild type controls (0.247 cm, p=0.414); while in week 6, mean LVDs was 0.321 cm in BCAA/Arg treated CIRS12KO mice, lower than saline-treated CIRS12KO mice (0.370 cm, p=0.007), but higher than wild type controls (0.270 cm, p=0.001). FIG. 3I illustrates that there was no significant difference between mean FS in week 4 and week 6 (24.27% vs. 22.75%, p=0.086). Mean FS in BCAA/Arg treated CIRS12KO mice (20.76%) was higher than that in saline-treated CIRS12KO mice (16.97%, p=0.001); however, it was lower than wild type controls (26.75%, p<0.001). A general linear model was used to compare the adjusted least square mean values of LVDs and FS. Left ventricular (LV) catheterization further revealed a significant increase in LV developed pressure (+34.7%) (FIG. 3J), and maximal rates of increase (FIG. 3K) and decrease (FIG. 3M) in LV pressure (+65.5%, +73.1% respectively, p<0.05 each) in CIRS12KO mice following BCAA/Arg treatment relative to saline treatment. Moreover, the increase in LV minimum pressure was completely prevented (FIG. 3L and Table 8). Thus, BCAA/Arg supplementation attenuated heart failure in CIRS12KO hearts.

Figure 3N:
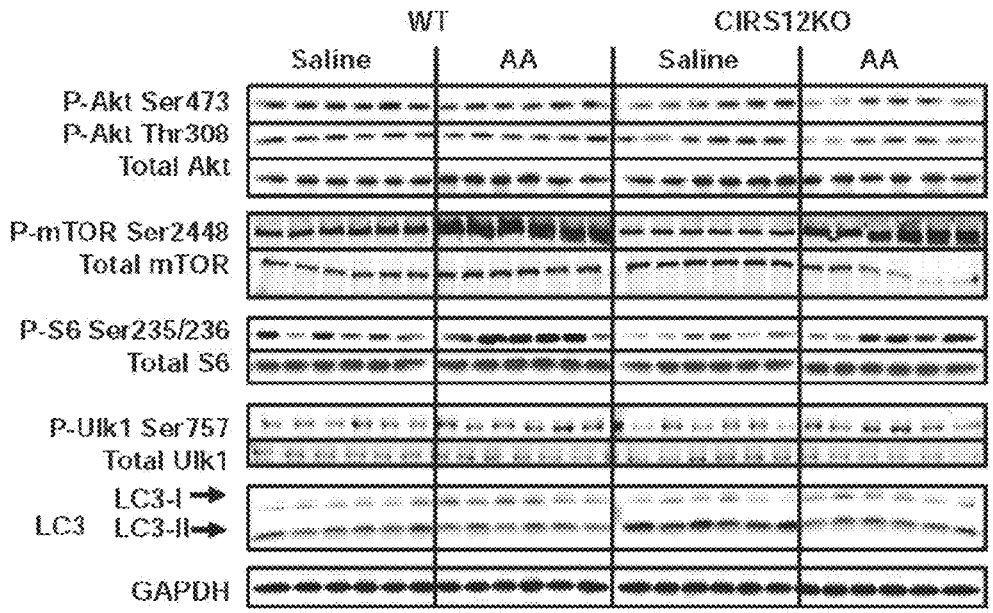
FIG. 3N is a representative immunoblot from ventricle homogenates obtained from CIRS12KO and wild type control mice following saline or BCAA/Arg (AA) treatment at the age of 2 weeks.
Figure 3O:
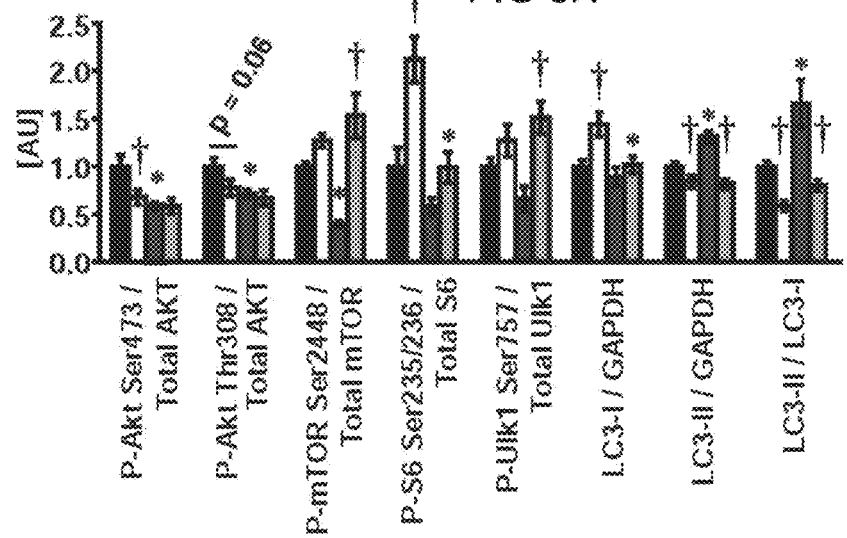
FIG. 3O is a graphical representation of densitometric quantification of the immunoblot of FIG. 3N.

Because heart failure per se may independently modulate signal transduction pathways, we examined two-week-old mice because contractile function was preserved in CIRS12KO hearts at this age (see FIG. 1K and Table 2). Importantly, BCAA/Arg treatment restored phosphorylation of mTOR (Ser2448), S6 (Ser235/236), Ulk1 (Ser757) and normalized LC3-II/LC3-I ratios to the physiological range observed in saline treated two-week-old WT mice (FIGS. 3N and 3O). These data support the hypothesis that BCAA/Arg supplementation suppresses autophagy in CIRS12KO hearts via mTOR mediated phosphorylation of Ulk1 (Ser757).

Prior studies suggest that BCAA/Arg supplementation may increase mitochondrial biogenesis and PGC-1α expression in cardiomyocytes. However BCAA/Arg treatment did not increase the expression levels of Pargc1a, Ppargc1b, or their transcriptional targets that regulate mitochondrial OXPHOS or FAO in wild type mice. Furthermore, relative to saline treated controls, BCAA/Arg supplementation had no effect on glucose tolerance, insulin tolerance and serum insulin levels following 20 weeks of treatment in wild type mice. In this experiment, saline or BCAA/Arg was administered to the mice starting the day of birth. Glucose tolerance tests, insulin tolerance tests, and plasma insulin levels were measured at the age of 20 weeks. Blood glucose was measured at the indicated time points post injection. No significant difference was observed between animals that were administered saline as compared to BCAA/Arg treatment (n=9-13).

In addition, contractile function, heart weight, and apoptotic cell death were measured in hearts dissected from the wild type mice. BCAA/Arg had no effect on these parameters relative to saline treatment.

TABLE 6

Heart weights and lung weights at 6 weeks of age following BCAA/Arg or Saline treatment

| Group | BW [g] | HW [mg] | TL [mm] | HW/BW [mg/g] |
|---|---|---|---|---|
| WT Sal | 18.31 ± 0.79 | 87.69 ± 3.90 | 15.10 ± 0.13 | 4.79 ± 0.05 |
| WT AA | 18.13 ± 0.95 | 92.47 ± 5.58 | 14.73 ± 0.23 | 5.10 ± 0.15 |
| CIRS12KO Sal | 15.66 ± 0.42 | 110.20 ± 3.30* | 14.88 ± 0.16 | 7.09 ± 0.38* |
| CIRS12KO AA | 17.07 ± 0.60† | 83.26 ± 3.56† | 14.84 ± 0.25 | 4.89 ± 0.17† |

| Group | HW/TL [mg/mm] | WLW [mg] | WLW/BW [mg/g] | WLW/TL [mg/mm] |
|---|---|---|---|---|
| WT Sal | 5.80 ± 0.23 | 125.86 ± 5.62 | 6.89 ± 0.21 | 8.33 ± 0.35 |
| WT AA | 6.27 ± 0.35 | 130.49 ± 3.93 | 7.27 ± 0.26 | 8.85 ± 0.20 |
| CIRS12KO Sal | 7.40 ± 0.21* | 238.39 ± 12.31* | 15.33 ± 1.02* | 16.01 ± 0.79* |
| CIRS12KO AA | 5.60 ± 0.71† | 122.11 ± 5.75† | 7.18 ± 0.32† | 8.23 ± 0.36† |

Data - mean values ± SEM are from male mice, n = 7,
*$p < 0.05$ vs. WT same treatment,
†$p < 0.05$ vs. Saline treatment same genotype (ANOVA/Fisher's PLSD);
Sal, Saline treatment;
AA, BCAA/Arg treatment;
BW, Body weight;
HW, Heart weight;
TL, Tibia length;
WLW, Wet lung weight.

TABLE 7

Contractile function assessed by transthoracic echocardiography following BCAA/Arg or Saline treatment

| Group | Age [Wk] | LVDd [cm] | LVDs [cm] | IVSDd [cm] |
|---|---|---|---|---|
| WT Sal | 4 | 0.351 ± 0.011 | 0.255 ± 0.008 | 0.062 ± 0.002 |
| WT AA | 4 | 0.329 ± 0.009 | 0.239 ± 0.010 | 0.063 ± 0.002 |
| CIRS12KO Sal | 4 | 0.384 ± 0.008 | 0.310 ± 0.008 | 0.051 ± 0.002 |
| CIRS12KO AA | 4 | 0.334 ± 0.005 | 0.256 ± 0.007 | 0.058 ± 0.002 |
| WT Sal | 5 | 0.361 ± 0.008 | 0.263 ± 0.008 | 0.069 ± 0.002 |
| WT AA | 5 | 0.365 ± 0.007 | 0.278 ± 0.007 | 0.062 ± 0.002 |
| CIRS12KO Sal | 5 | 0.426 ± 0.004 | 0.361 ± 0.006 | 0.052 ± 0.001 |
| CIRS12KO AA | 5 | 0.376 ± 0.005 | 0.304 ± 0.006 | 0.054 ± 0.002 |
| WT Sal | 6 | 0.371 ± 0.007 | 0.273 ± 0.005 | 0.066 ± 0.002 |
| WT AA | 6 | 0.373 ± 0.011 | 0.267 ± 0.011 | 0.067 ± 0.003 |
| CIRS12KO Sal | 6 | 0.441 ± 0.009 | 0.370 ± 0.008 | 0.057 ± 0.004 |
| CIRS12KO AA | 6 | 0.398 ± 0.011 | 0.321 ± 0.016 | 0.055 ± 0.002 |

| Group | IVSDs [cm] | LVPWd [cm] | LVPWs [cm] | FS [%] | EF [%] |
|---|---|---|---|---|---|
| WT Sal | 0.090 ± 0.003 | 0.056 ± 0.002 | 0.080 ± 0.004 | 61.60 ± 1.07 | 27.35 ± 0.68 |
| WT AA | 0.089 ± 0.004 | 0.056 ± 0.001 | 0.073 ± 0.002 | 61.42 ± 2.14 | 27.43 ± 1.46 |
| CIRS12KO Sal | 0.070 ± 0.003 | 0.053 ± 0.002 | 0.069 ± 0.004 | 47.10 ± 2.09 | 19.20 ± 1.08 |
| CIRS12KO AA | 0.082 ± 0.002 | 0.055 ± 0.003 | 0.071 ± 0.005 | 54.77 ± 2.28 | 23.38 ± 1.38 |
| WT Sal | 0.100 ± 0.004 | 0.056 ± 0.001 | 0.075 ± 0.002 | 61.30 ± 1.74 | 27.23 ± 1.11 |
| WT AA | 0.090 ± 0.003 | 0.059 ± 0.002 | 0.078 ± 0.003 | 55.35 ± 2.03 | 23.72 ± 1.17 |
| CIRS12KO Sal | 0.069 ± 0.003 | 0.050 ± 0.001 | 0.065 ± 0.004 | 39.28 ± 2.09 | 15.38 ± 0.99 |
| CIRS12KO AA | 0.074 ± 0.002 | 0.050 ± 0.002 | 0.063 ± 0.003 | 47.32 ± 1.63 | 19.29 ± 0.82 |
| WT Sal | 0.095 ± 0.003 | 0.058 ± 0.001 | 0.079 ± 0.002 | 59.89 ± 0.63 | 26.27 ± 0.39 |
| WT AA | 0.102 ± 0.004 | 0.060 ± 0.003 | 0.085 ± 0.004 | 63.22 ± 1.66 | 28.48 ± 1.09 |
| CIRS12KO Sal | 0.075 ± 0.004 | 0.055 ± 0.005 | 0.071 ± 0.006 | 40.38 ± 2.39 | 15.92 ± 1.15 |
| CIRS12KO AA | 0.079 ± 0.005 | 0.055 ± 0.003 | 0.070 ± 0.004 | 47.52 ± 3.76 | 19.62 ± 1.93 |

Data - mean values ± SEM are from male mice, n = 6-9,
LVDd, Left ventricular cavity diameter at diastole;
LVDs, Left ventricular cavity diameter at systole;
IVSDd, Interventricular septum diameter at diastole;
IVSDs, Interventricular septum diameter at systole;
LVPWd, Left ventricular posterior wall thickness at diastole;
LVPWs, Left ventricular posterior wall thickness at systole;
FS, Fractional shortening;
EF, Ejection fraction.

TABLE 8

Invasive measurement of left ventricular pressures at six weeks of age following BCAA/Arg or Saline treatment as assessed by catheterization

| Group | LVSP [mmHg] | LVMP [mmHg] |
|---|---|---|
| WT Sal | 92.11 ± 2.29 | 4.04 ± 2.37 |
| WT AA | 94.97 ± 4.40 | 2.99 ± 2.45 |
| CIRS12KO Sal | 62.07 ± 3.20* | 15.10 ± 1.59* |
| CIRS12KO AA | 77.35 ± 3.96*† | 5.53 ± 2.64† |

| Group | LV Dev P [mmHg] | Heart Rate [bpm] | Max dP/dt [mmHg/s] | Min dP/dt [mmHg/s] |
|---|---|---|---|---|
| WT Sal | 88.07 ± 3.09 | 553.06 ± 18.15 | 7036.03 ± 546.65 | −6362.95 ± 474.97 |
| WT AA | 91.98 ± 5.97 | 600.24 ± 12.98 | 8038.32 ± 613.12 | −7602.14 ± 646.50 |
| CIRS12KO Sal | 46.97 ± 2.70* | 583.82 ± 25.66 | 2596.50 ± 152.57* | −2628.74 ± 145.02* |
| CIRS12KO AA | 71.82 ± 5.72*† | 639.73 ± 12.47† | 4760.06 ± 677.12*† | −5328.42 ± 1115.04*† |

Data - mean values ± SEM are from male mice,
*p <0.05 vs. same Beclin genotype,
†p <0.05 vs. same IRS genotype (ANOVA/Fisher's PLSD).
BW, Body weight;
HW, Heart weight;
TL, Tibia length;
WLW, Wet lung weight;
n.d.; not determined.

Figure 4M:
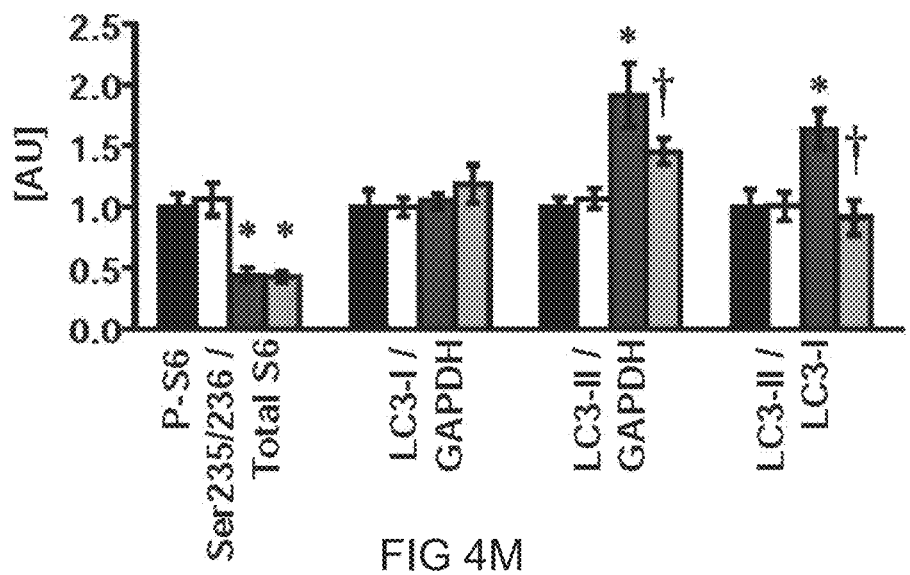
FIG. 4M is a graph representing quantification of immunoblots from ventricle homogenates obtained from 2 week old mice having the indicated genotypes (n=6).
Figures 4N, 4O, 4P:
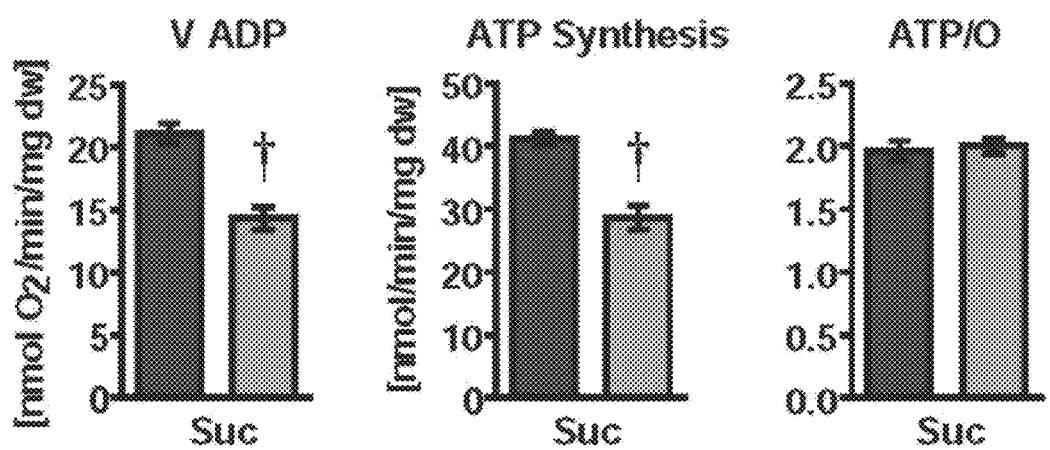
FIG. 4N is a graph illustrating impaired VADP respiration in cardiac fibers from 2 week old CIRS12KO×Bec+/− mice with Succinate/Rotenone as substrate (n=6).
FIG. 4O is a graph illustrating impaired ATP-production in tissues described in FIG. 4M.
FIG. 4P is a graph illustrating ATP/O in tissues described in FIG. 4M.
Figure 4Q:
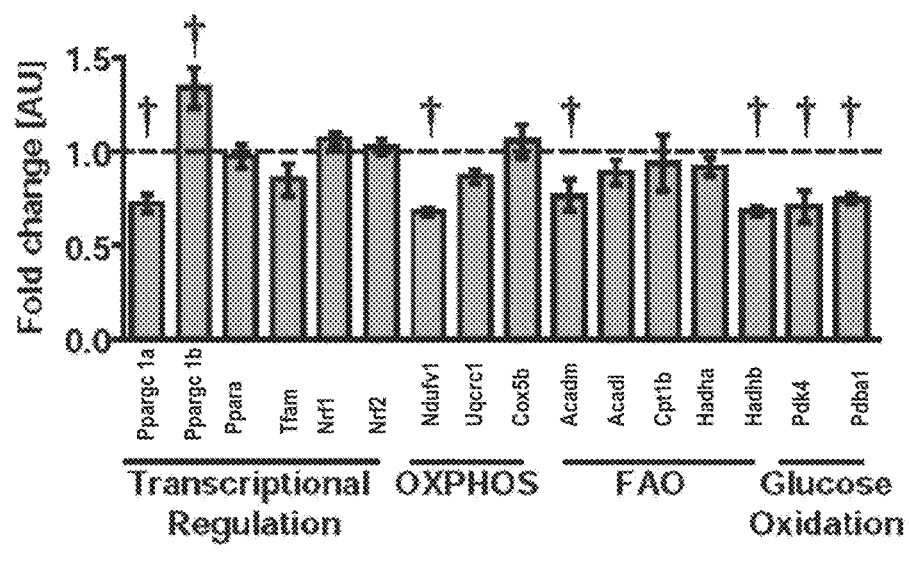
FIG. 4Q is a graph illustrating quantification of immunoblots indicating gene expression in hearts of 2 week old CIRS12KO×Beclin+/− mice as indicated (n=6).

To independently confirm that decreasing autophagy is necessary and sufficient to reverse heart failure in CIRS12KO mice, autophagy levels in CIRS12KO mouse hearts were reduced by crossing them with mice that are haploinsufficient for Beclin1 (IRS1lox/lox:IRS2lox/lox: αMHC-Cre+/−: Bec+/−). Beclin 1 is required for autophagosome formation and heterozygous deletion of Beclin1 decreases autophagy. Similar to BCAA/Arg treatment, heterozygous deletion of Beclin1 extended the lifespan of CIRS12KO mice, prevented the increase in heart and lung weights, diminished left ventricular dilation, improved contractile function, and decreased cardiomyocyte loss and replacement fibrosis at six weeks of age (FIGS. 4A-L and Tables 9-11). FIG. 4B illustrates that heterozygous deletion of Beclin1 increased the average lifespan of CIRS12KO mice from 7.4 to 16.8 weeks (p<0.0001, Log-rank Test). FIG. 4G illustrates that mean LVDs in week 4 was significantly lower than week 6 (0.254 cm vs. 0.291 cm, p<0.001). Mean LVDs in CIRS12KO×Bec+/− (0.274 cm) was statistically lower than CIRS12KO mice (0.322 cm, p<0.001), although it was still higher than wild type×Bec+/− (0.249 cm, p=0.037) and WT controls (0.245 cm, p=0.010). FIG. 4H shows that mean fractional shortening (FS) in week 4 was not statistically different from week 6 (26.25% vs. 24.69%, p=0.161). Mean FS in CIRS12KO×Bec+/− het (24.81%) was statistically higher than CIRS12KO mice (18.96%, p<0.001), although it was still lower than WT×Bec+/− (28.79%, p=0.025) and WT controls (29.32%, p=0.003). A general linear model with Tukey-Kramer multiple comparison adjustment was used to compare the adjusted least square mean values of LVDs and FS. Western Blot analysis at the two-week time point revealed decreased autophagy in CIRS12KO hearts following heterozygous deletion of Beclin1 despite reduced mTOR signaling (FIG. 4M). CIRS12KO×Bec+/− exhibited mitochondrial dysfunction as assessed in protein detection in saponin-permeabilized cardiac fibers (FIGS. 4N-P) and mRNA-expression of Ppargc1a and genes involved in FAO and OXPHOS were reduced (FIG. 4Q). Data in FIG. 4Q are presented as fold change vs. Beclin+/− (=1.0, Gapdh was used for normalization). *p<0.05 vs. same Beclin genotype, t p<0.05 vs. same IRS genotype. Gene names are shown in Table 1. Thus, despite increased survival and delayed heart failure onset, heart failure eventually developed in CIRS12KO when the over-activation of autophagy was prevented. Therefore, additional mechanisms arising from reduced insulin signaling, such as mitochondrial dysfunction and increased apoptosis, contribute to the development of heart failure in CIRS12KO hearts.

TABLE 9

Heart weights and lung weights at 2 and 6 weeks of age in Bec[+/−] CIRS12KO Cross

| Group (n) | Age [wk] | BW [g] | HW [mg] | TL [mm] |
|---|---|---|---|---|
| WT (6) | 2 | 7.68 ± 0.93 | 43.73 ± 4.96 | n.d. |
| WT × Bec[+/−] (6) | 2 | 7.10 ± 0.47 | 42.05 ± 1.89 | |
| CIRS12KO (6) | 2 | 8.82 ± 0.68 | 48.55 ± 2.86 | |
| CIRS12KO × Bec[+/−] (6) | 2 | 7.59 ± 0.47 | 39.78 ± 2.75 | |
| WT (6) | 6 | 18.78 ± 0.58 | 91.17 ± 3.34 | 15.38 ± 0.13 |
| WT × Bec[+/−] (7) | 6 | 19.07 ± 0.89 | 89.71 ± 4.68 | 15.31 ± 0.26 |
| CIRS12KO (6) | 6 | 19.82 ± 0.48 | 97.83 ± 5.02 | 15.50 ± 0.15 |
| CIRS12KO × Bec[+/−] (10) | 6 | 17.91 ± 0.58 | 85.80 ± 2.24† | 15.07 ± 0.19 |

TABLE 9-continued

Heart weights and lung weights at 2 and 6 weeks of age in Bec$^{+/-}$ CIRS12KO Cross

| Group (n) | HW/BW [mg/g] | HW/TL [mg/mm] | WLW [mg] | WLW/BW [mg/g] | WLW/TL [mg/mm] |
|---|---|---|---|---|---|
| WT (6) | 5.79 ± 0.40 | n.d. | n.d. | n.d. | n.d. |
| WT × Bec$^{+/-}$ (6) | 6.01 ± 0.35 | | | | |
| CIRS12KO (6) | 5.59 ± 0.27 | | | | |
| CIRS12KO × Bec$^{+/-}$ (6) | 5.28 ± 0.34 | | | | |
| WT (6) | 4.86 ± 0.12 | 5.92 ± 0.19 | 134.17 ± 1.80 | 7.17 ± 0.16 | 8.72 ± 0.08 |
| WT × Bec$^{+/-}$ (7) | 4.70 ± 0.11 | 5.84 ± 0.23 | 135.57 ± 7.19 | 7.11 ± 0.18 | 8.83 ± 0.38 |
| CIRS12KO (6) | 4.93 ± 0.18 | 6.32 ± 0.36 | 182.17 ± 9.21* | 9.20 ± 0.44* | 11.77 ± 0.66* |
| CIRS12KO × Bec$^{+/-}$ (10) | 4.83 ± 0.19 | 5.69 ± 0.13† | 137.20 ± 7.47† | 7.79 ± 0.66 | 9.10 ± 0.49† |

Data - mean values ± SEM are from male mice,
*p <0.05 vs. same Beclin genotype,
†p <0.05 vs. same IRS genotype (ANOVA/Fisher's PLSD).
BW, Body weight;
HW, Heart weight;
TL, Tibia length;
WLW, Wet lung weight;
n.d.; not determined.

TABLE 10

Invasive measurement of left ventricular pressures at six weeks of age as assessed by catheterization in Bec$^{+/-}$ CIRS12KO

| Group (n) | LVSP [mmHg] | LVMP [mmHg] | LV Dev P [mmHg] |
|---|---|---|---|
| WT (6) | 94.63 ± 2.37 | 5.43 ± 1.10 | 89.19 ± 3.12 |
| WT × Bec$^{+/-}$ (6) | 102.78 ± 3.17 | 3.45 ± 1.06 | 90.33 ± 3.04 |
| CIRS12KO (7) | 75.71 ± 1.97* | 13.48 ± 1.48* | 62.23 ± 2.39* |
| CIRS12KO × Bec$^{+/-}$ (10) | 90.48 ± 4.57*† | 6.68 ± 1.23† | 83.80 ± 5.50*† |

| Group (n) | Heart Rate [bpm] | Max dP/dt [mmHg/s] | Min dP/dt [mmHg/s] |
|---|---|---|---|
| WT (6) | 513.23 ± 7.77 | 7192.17 ± 359.39 | −6949.82 ± 581.30 |
| WT × Bec$^{+/-}$ (6) | 529.91 ± 13.04 | 7978.80 ± 381.46 | −8249.27 ± 389.16 |
| CIRS12KO (7) | 547.91 ± 21.55 | 3890.94 ± 283.27* | −3682.20 ± 287.24* |
| CIRS12KO × Bec$^{+/-}$ (10) | 508.43 ± 13.90 | 6438.89 ± 684.55† | −6375.12 ± 722.66*† |

Data - mean values ± SEM are from male mice,
*p <0.05 vs. same Beclin genotype,
†p <0.05 vs. same IRS genotype (ANOVA/Fisher's PLSD).
LVSP, left ventricular systolic pressure;
LVMP, left ventricular minimum pressure;
LV Dev P, left ventricular developed pressure;
bpm, beats per minute;
Max dP/dt, maximal rate of increase in left ventricular pressure;
Min dP/dt, maximal rate of decrease in left ventricular pressure

TABLE 11

Contractile function assessed by transthoracic echocardiography in Bec$^{+/-}$ CIRS12KO Cross

| Group | Age [Wk] | LVDd [cm] | LVDs [cm] | IVSDd [cm] |
|---|---|---|---|---|
| WT | 4 | 0.329 ± 0.009 | 0.229 ± 0.009 | 0.072 ± 0.001 |
| WT × Bec$^{+/-}$ | 4 | 0.341 ± 0.011 | 0.250 ± 0.010 | 0.069 ± 0.002 |
| CIRS12KO | 4 | 0.356 ± 0.013 | 0.282 ± 0.018 | 0.060 ± 0.003 |
| CIRS12KO × Bec$^{+/-}$ | 4 | 0.342 ± 0.005 | 0.253 ± 0.008 | 0.063 ± 0.002 |
| WT | 6 | 0.363 ± 0.008 | 0.262 ± 0.010 | 0.075 ± 0.004 |
| WT × Bec$^{+/-}$ | 6 | 0.359 ± 0.008 | 0.250 ± 0.008 | 0.073 ± 0.002 |
| CIRS12KO | 6 | 0.425 ± 0.013 | 0.352 ± 0.013 | 0.059 ± 0.002 |
| CIRS12KO × Bec$^{+/-}$ | 6 | 0.386 ± 0.011 | 0.296 ± 0.013 | 0.067 ± 0.002 |
| WT | 12 | 0.384 ± 0.013 | 0.274 ± 0.014 | 0.071 ± 0.003 |
| WT × Bec$^{+/-}$ | 12 | 0.363 ± 0.009 | 0.257 ± 0.012 | 0.074 ± 0.003 |
| CIRS12KO × Bec$^{+/-}$ | 12 | 0.476 ± 0.014 | 0.401 ± 0.016 | 0.055 ± 0.005 |

TABLE 11-continued

Contractile function assessed by transthoracic echocardiography in Bec$^{+/-}$ CIRS12KO Cross

| Group | IVSDs [cm] | LVPWd [cm] | LVPWs [cm] | FS [%] | EF [%] |
|---|---|---|---|---|---|
| WT | 0.099 ± 0.002 | 0.058 ± 0.001 | 0.082 ± 0.002 | 66.57 ± 1.14 | 30.66 ± 0.77 |
| WT × Bec$^{+/-}$ | 0.089 ± 0.003 | 0.062 ± 0.002 | 0.081 ± 0.005 | 60.48 ± 3.09 | 26.88 ± 1.95 |
| CIRS12KO | 0.079 ± 0.005 | 0.053 ± 0.003 | 0.066 ± 0.004 | 50.60 ± 3.93 | 21.18 ± 2.13 |
| CIRS12KO × Bec$^{+/-}$ | 0.084 ± 0.004 | 0.057 ± 0.002 | 0.078 ± 0.003 | 59.03 ± 2.52 | 26.00 ± 1.48 |
| WT | 0.102 ± 0.007 | 0.065 ± 0.002 | 0.089 ± 0.003 | 62.14 ± 2.80 | 28.04 ± 1.75 |
| WT × Bec$^{+/-}$ | 0.105 ± 0.004 | 0.065 ± 0.003 | 0.092 ± 0.002 | 66.01 ± 1.64 | 30.32 ± 1.13 |
| CIRS12KO | 0.074 ± 0.001 | 0.053 ± 0.001 | 0.069 ± 0.002 | 43.50 ± 2.14 | 17.46 ± 1.07 |
| CIRS12KO × Bec$^{+/-}$ | 0.089 ± 0.004 | 0.059 ± 0.002 | 0.078 ± 0.004 | 54.85 ± 2.95 | 23.58 ± 1.71 |
| WT | 0.097 ± 0.004 | 0.064 ± 0.003 | 0.088 ± 0.003 | 63.65 ± 2.61 | 28.79 ± 1.65 |
| WT × Bec$^{+/-}$ | 0.104 ± 0.006 | 0.069 ± 0.003 | 0.088 ± 0.006 | 64.22 ± 2.82 | 29.21 ± 1.90 |
| CIRS12KO × Bec$^{+/-}$ | 0.069 ± 0.006 | 0.050 ± 0.004 | 0.066 ± 0.006 | 40.05 ± 3.11 | 15.78 ± 1.47 |

Data - mean values ± SEM are from male mice, n = 5-10,
LVDd, Left ventricular cavity diameter at diastole;
LVDs, Left ventricular cavity diameter at systole;
IVSDd, Interventricular septum diameter at diastole;
IVSDs, Interventricular septum diameter at systole;
LVPWd, Left ventricular posterior wall thickness at diastole;
LVPWs, Left ventricular posterior wall thickness at systole;
FS, Fractional shortening;
EF, Ejection fraction

TABLE 12

Metabolic Profile of Serum, heart, and Liver Tissue Following 20 Weeks of BCAA/Arg Supplementation

| | Serum | Heart | Liver |
|---|---|---|---|
| SUPERPATHWAY | | | |
| SubPathway | | | |
| Metabolite | | | |
| ENERGY | | | |
| TCA Cycle | | | |
| Citrate | 1.21* | 0.78 | 0.94 |
| Isocitrate | 1.33 | 0.87 | 0.84 |
| Aconitate | 1.51* | 0.55† | 1.20 |
| α-Ketoglutarate | 0.57† | 0.46 | 0.90 |
| Succinate | 0.93 | 1.25 | 1.35 |
| Fumarate | 1.23 | 1.04 | 0.35 |
| Malate | 1.13 | 1.07 | 1.34 |
| Oxidative Phosphorylation | | | |
| Phosphate | 1.22 | 1.01 | 1.07 |
| Diphosphate | 1.45 | 1.05 | 1.48 |
| CARBOHYDRATE | | | |
| Glycolysis and Pyruvate Metabolism | | | |
| Glucose | 0.76 | 0.93 | 0.94 |
| Glucose-6-phosphate | n.d. | 1.24 | 0.78 |
| Glucose-1-phosphate | n.d. | 1.23 | 0.72 |
| 3-Phosphoglycerate | 0.79 | 1.07 | 0.70 |
| 2-Phosphoglycerate | n.d. | n.d. | 0.74 |
| Glycerate | 1.14 | 0.54 | 0.45 |
| Pyruvate | 0.82 | 0.84 | 0.88 |
| Lactate | 1.15 | 1.28 | 1.09 |
| Fructose, Mannose, Sucrose, and Galactose Metabolism | | | |
| Fructose | 0.37 | 1.16 | 1.14 |
| Fructose-6-phosphate | n.d. | 1.08 | 1.13 |
| Mannitol | 2.54* | 1.07 | 2.66* |
| Galactose | 0.81 | 0.97 | 1.22 |
| Sucrose | 1.48 | 1.50 | 1.07 |
| Galactitol | n.d. | 1.10 | n.d. |
| Nucleotide Sugars, Pentose Metabolism | | | |
| Ribose | 1.05 | 1.09 | 0.84 |
| Ribose-5'-phosphate | n.d. | 1.17 | 0.94 |
| Other Sugars | | | |
| Sorbitol | 1.51 | 1.27 | 0.99 |
| AMINO ACID | | | |
| Alanine and Aspartate Metabolism | | | |
| beta-Alanine | 1.33 | n.d. | 0.81 |
| Alanine | 1.06 | 0.76 | 0.88 |
| Aspartate | 1.48* | 1.06 | 1.05 |
| Creatine Metabolism | | | |
| Creatine | 1.34* | 1.08 | 1.40* |
| Cysteine and Methionine Metabolism | | | |
| Taurine | 1.78* | 0.99 | 1.13 |
| Methionine | 0.68 | 0.60 | 1.29 |
| Cysteine | 0.94 | 0.63 | 0.91 |
| Glutamate Metabolism | | | |
| Glutamate | 1.54 | 1.14 | 1.12 |
| Glutamine | 1.33* | 2.03 | 0.80 |
| Glutathione Metabolism | | | |
| GSH (reduced glutathione) | n.d. | 1.18 | 0.99 |
| Asparagine | 0.98 | 0.26 | 4.14 |
| Glycine, Serine, and Threonine Metabolism | | | |
| Glycine | 0.85† | 0.80† | 0.64† |
| Serine | 0.94 | 0.35† | 0.91 |
| Threonine | 0.66† | 0.47† | 0.92 |
| Histidine Metabolism | | | |
| Histidine | 0.65 | 0.36 | 0.63 |
| Lysine Metabolism | | | |
| Lysine | 0.87† | n.d. | 0.80 |
| 2-Aminoadipic acid | n.d. | 0.58 | 0.40 |

TABLE 12-continued

Metabolic Profile of Serum, heart, and Liver Tissue
Following 20 Weeks of BCAA/Arg Supplementation

| | Serum | Heart | Liver |
|---|---|---|---|
| Phenylalanine and Tyrosine Metabolism | | | |
| Phenylalanine | 0.90 | 0.91 | 1.25 |
| Tyrosine | 0.58† | n.d. | 2.04 |
| Tryptophan Metabolism | | | |
| Tryptophan | 0.87 | n.d. | n.d. |
| Valine, Leucine, and Isoleucine Metabolism | | | |
| Isoleucine | 1.50* | 1.17* | 1.64* |
| Leucine | 1.94* | 1.50* | 1.86* |
| Valine | 2.25* | 1.59* | 2.32* |
| Homoserine | 1.53 | 0.87 | 1.32 |
| Urea Cycle, Arginine and Proline Metabolism | | | |
| Urea | 1.54* | 2.12* | 1.79* |
| Proline | 1.02 | 0.72 | 1.52* |
| Arginine | 2.96* | 1.52* | n.d. |
| Hydroxyproline | n.d. | 0.41† | 1.34 |
| Ornithine | 0.31† | n.d. | 0.93 |
| LIPID | | | |
| Essential Fatty Acid | | | |
| Linoleate (18:2n6) | 0.88 | 0.96 | 1.06 |
| Medium Chain Fatty Acid | | | |
| Laureate (12:0) | 0.78 | 0.85 | 1.01 |
| Long Chain Fatty Acid | | | |
| Myristate (14:0) | 0.82 | 1.22 | 0.98 |
| Palmitate (16:0) | 1.02 | 1.13 | 1.02 |
| Stearate (18:0) | 1.02 | 1.08 | 1.04 |
| Oleate (18:1n9) | 0.95 | 1.03 | 1.17 |
| Elaidicate (18:1n9) | 0.99 | 0.99 | 1.20 |
| Arachidonate (20:4n6) | 0.80 | 1.10 | 1.02 |
| Sterol/Steroid Metabolism | | | |
| Cholesterol | 1.10 | 1.02 | 0.96 |
| Glycerolipid Metabolism | | | |
| Glycerol | 1.54 | 1.46* | 1.31 |
| Choline | 1.16 | 0.87 | 1.39 |
| 1-Monooleoylglycerol | 1.09 | 0.87 | 0.88 |
| 1-Monostearylglycerol | 1.37* | 0.92 | 0.90 |
| 2-Monostearylglycerol | 1.14 | 0.91 | 0.84 |
| 1-Monopalmitoylglycerol | 1.53* | 0.98 | 1.05 |
| 1-Monopalmitolylglycerol | n.d. | 0.76 | n.d. |
| Carnitine Metabolism | | | |
| Carnitine | 1.05 | 0.96 | 1.19 |
| Carnitine (16:0) | 1.20 | 1.16 | 1.87* |
| Carnitine (16:1) | 0.90 | 1.22 | 1.16 |
| Carnitine (18:0) | 1.02 | 1.27 | 2.12* |
| Carnitine (18:1) | 0.90 | 1.48 | 2.13* |
| Carnitine (18:2) | 0.92 | 1.67 | 2.18* |
| Carnitine (18:3) | 1.26 | 1.73 | 1.94* |
| Acetyl-Carnitine | 1.18 | 0.52 | 1.51* |
| (Iso)-Butyl-Carnitine | 2.17* | 1.86* | 3.22* |
| Inositol Metabolism | | | |
| Myo-inositol phosphate | 1.02 | 1.03 | 1.48 |
| Inositol | 1.50* | 0.92 | 1.04 |
| Ketone Bodies | | | |
| 3-Hydroxybutyrate | 1.15 | 1.56 | 1.29 |
| NUCELOTIDE | | | |
| Purine Metabolism, (Hypo)xanthine/Inosine Containing | | | |
| Hypoxanthine | 2.02 | n.d. | 0.60 |
| Inosine | 1.27 | n.d. | 0.86 |
| Purine Metabolism, Adenine Containing | | | |
| Adenosine | 0.66 | 0.73 | 1.47 |
| Adenine | 0.48† | 0.79 | 0.88 |
| AMP (adenosine 5'-monophosphate) | 1.77 | 1.08 | 0.86 |
| Pyrimidine Metabolism, Urate Containing | | | |
| Urate | 0.89 | n.d. | 0.82 |
| Pyrimidine Metabolism, Uracil Containing | | | |
| Uracil | 0.88 | 1.27* | 1.54 |

Data are presented as fold change compared to Saline treated controls.
Footnoted (* and †) cells indicate a significant difference compared to Saline treated controls (* = increased, † = decreased, Unpaired Student's t-test, n = 6-11).

Two independent approaches were used to suppress autophagy in CIRS12KO hearts. Pharmacological activation of mTOR signaling by BCAA/Arg supplementation and heterozygote deletion of Beclin 1 decreased autophagy in CIRS12KO hearts to levels observed in WT controls. This delayed the onset of heart failure and prolonged the lifespan of CIRS12KO mice. Together, these data support an essential role for excessive autophagy in the pathophysiology of heart failure in CIRS12KO mice and support an essential role for insulin signaling as a critical physiological regulator of perinatal cardiac autophagy.

A mouse model with combined deficiency of insulin and IGF-1 receptors in cardiac and skeletal muscle has been previously described in the art. Similar to CIRS12KO, these mutant mice developed early onset dilated cardiomyopathy and died from heart failure within the first month of life. This study suggests mitochondrial dysfunction as a cause for heart failure. Mitochondrial dysfunction was also observed in CIRS12KO hearts at the age of two weeks that was not improved by heterozygous deletion of Beclin1 (FIGS. 1N-P and FIGS. 4N-P). Because mitochondrial dysfunction preceded contractile dysfunction, it likely also contributes to the onset of heart failure. Changes observed in the mitochondrial proteome and mitochondrial energetics in 4-week-old CIRS12KO mice are more severe than those that were previously reported in a model of pressure overload induced heart failure. These data are consistent with a model in which mitochondrial dysfunction may not only incite heart failure, but is progressively impaired as heart failure ensues.

In conclusion, the study disclosed herein identifies IRS signaling as a critical physiological regulator of perinatal cardiac autophagy and of mitochondrial function in the heart. The inability to sense nutrients promotes uncontrolled autophagy and blunts the developmental increase in mitochondrial energetic capacity leading to myocyte loss and heart failure. Thus insulin/IGF1 signaling through IRS-proteins represents an important mediator of the perinatal maturation of cardiac metabolic pathways, linking nutrient availability to postnatal cardiac development.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

The invention claimed is:

1. A formulation comprising:
   a medically useful amount of L-isoleucine, L-leucine, L-valine, and L-arginine wherein the relative ratio of L-isoleucine:L-leucine:L-valine, by mass, is 1:2(±0.2):1.2(±0.2),
   wherein the medically useful amount of L-isoleucine, L-leucine, L-valine, and L-arginine is dissolved in an aqueous solvent to form a solution; and
   wherein the osmolarity of the solution is below 325 mosm.

2. The formulation of claim 1, wherein the relative ratio, by mass, of L-isoleucine:L-leucine:L-valine:L-arginine is about 1:2(±0.2):1.2(±0.2):1(±0.2).

3. The formulation of claim 1, wherein L-isoleucine is present in a concentration of 6 g/L (±0.3 g/L), L-leucine is present in a concentration of 12 g/L (±0.3 g/L), L-valine is present in a concentration of 7.2 g/L (±0.3 g/L), and L-arginine is present in a concentration of 6.04 g/L (±0.3 g/L).

4. The formulation of claim 1, wherein the pH of the formulation is buffered to a physiologically tolerable pH.

5. The formulation of claim 4, wherein the pH of the formulation is about 7.4.

6. The formulation of claim 4, wherein the formulation is buffered with a phosphate buffer.

7. The formulation of claim 1, wherein the formulation is sterile and pyrogen-free.

8. A kit comprising:
   (a) a lyophilized formulation comprising a medically useful amount of L-isoleucine, L-leucine, L-valine, and L-arginine, wherein the relative ratio of L-isoleucine:L-leucine:L-valine, by mass, is 1:2(±0.2):1.2(±0.2);
   (b) a vial or ampoule of a sterile aqueous solution; and
   (c) instructions for combining the lyophilized formulation with the sterile aqueous solution to form a solution having an osmolarity below 325 mosm.

9. The kit of claim 8, further comprising an injection device for administration.

10. The formulation of claim 1, wherein L-isoleucine, L-leucine, L-valine, and L-arginine are the only amino acids in the solution.

* * * * *

SEQUENCE LISTING

<160> NUMBER OF SEQ ID NOS: 74

<210> SEQ ID NO 1
<211> LENGTH: 20
<212> TYPE: DNA
<213> ORGANISM: Mus musculus

<400> SEQUENCE: 1
cctgtatgcc aacaacgtca                                          20

<210> SEQ ID NO 2
<211> LENGTH: 20
<212> TYPE: DNA
<213> ORGANISM: Mus musculus

<400> SEQUENCE: 2
ctcgtcgtac tcctgcttgg                                          20

<210> SEQ ID NO 3
<211> LENGTH: 20
<212> TYPE: DNA
<213> ORGANISM: Mus musculus

<400> SEQUENCE: 3
atggcaaaat actgggcatc                                          20

<210> SEQ ID NO 4
<211> LENGTH: 20
<212> TYPE: DNA
<213> ORGANISM: Mus musculus

<400> SEQUENCE: 4
tcttgcgatc agctctttca                                          20

<210> SEQ ID NO 5
<211> LENGTH: 20
<212> TYPE: DNA
<213> ORGANISM: Mus musculus

<400> SEQUENCE: 5
actgacgccg ttcagatttt                                          20

<210> SEQ ID NO 6
<211> LENGTH: 22
<212> TYPE: DNA
<213> ORGANISM: Mus musculus

<400> SEQUENCE: 6
gcttagttac acgagggtga tg                                       22

<210> SEQ ID NO 7
<211> LENGTH: 19
<212> TYPE: DNA
<213> ORGANISM: Mus musculus

<400> SEQUENCE: 7
ttggcgagaa aaacagcac                                           19

<210> SEQ ID NO 8
<211> LENGTH: 20
<212> TYPE: DNA
<213> ORGANISM: Mus musculus

<400> SEQUENCE: 8
gctgagaaaa ttcccccttt                                              20

<210> SEQ ID NO 9
<211> LENGTH: 20
<212> TYPE: DNA
<213> ORGANISM: Mus musculus

<400> SEQUENCE: 9
tgcctttaca tcgtctccaa                                              20

<210> SEQ ID NO 10
<211> LENGTH: 19
<212> TYPE: DNA
<213> ORGANISM: Mus musculus

<400> SEQUENCE: 10
agaccccgta gccatcatc                                               19

<210> SEQ ID NO 11
<211> LENGTH: 23
<212> TYPE: DNA
<213> ORGANISM: Mus musculus

<400> SEQUENCE: 11
agcactggag agaaaggatt tgg                                          23

<210> SEQ ID NO 12
<211> LENGTH: 22
<212> TYPE: DNA
<213> ORGANISM: Mus musculus

<400> SEQUENCE: 12
tcttcttgct ggtcttgcca tt                                           22

<210> SEQ ID NO 13
<211> LENGTH: 20
<212> TYPE: DNA
<213> ORGANISM: Mus musculus

<400> SEQUENCE: 13
cgctgaagga gaaggagaag                                              20

<210> SEQ ID NO 14
<211> LENGTH: 20
<212> TYPE: DNA
<213> ORGANISM: Mus musculus

<400> SEQUENCE: 14
gcagtgaagc caatgaagaa                                              20

<210> SEQ ID NO 15
<211> LENGTH: 20
<212> TYPE: DNA
<213> ORGANISM: Mus musculus

<400> SEQUENCE: 15
tggaggtggt gtccctactg                                              20

<210> SEQ ID NO 16
<211> LENGTH: 20
<212> TYPE: DNA
<213> ORGANISM: Mus musculus

```
<400> SEQUENCE: 16
ctcttgttgc tgatggatgg                                              20

<210> SEQ ID NO 17
<211> LENGTH: 20
<212> TYPE: DNA
<213> ORGANISM: Mus musculus

<400> SEQUENCE: 17
ggaggacggc agaagtacaa                                              20

<210> SEQ ID NO 18
<211> LENGTH: 20
<212> TYPE: DNA
<213> ORGANISM: Mus musculus

<400> SEQUENCE: 18
caggttcaac aaccagcaga                                              20

<210> SEQ ID NO 19
<211> LENGTH: 20
<212> TYPE: DNA
<213> ORGANISM: Mus musculus

<400> SEQUENCE: 19
aggtgggcac tctggttttt                                              20

<210> SEQ ID NO 20
<211> LENGTH: 20
<212> TYPE: DNA
<213> ORGANISM: Mus musculus

<400> SEQUENCE: 20
ataggctcaa tcccgtcctt                                              20

<210> SEQ ID NO 21
<211> LENGTH: 19
<212> TYPE: DNA
<213> ORGANISM: Mus musculus

<400> SEQUENCE: 21
cgtaggacgc aatgatgct                                               19

<210> SEQ ID NO 22
<211> LENGTH: 22
<212> TYPE: DNA
<213> ORGANISM: Mus musculus

<400> SEQUENCE: 22
tgttcacaaa attcaaggca ga                                           22

<210> SEQ ID NO 23
<211> LENGTH: 20
<212> TYPE: DNA
<213> ORGANISM: Mus musculus

<400> SEQUENCE: 23
gacgggaaac tcatcctgac                                              20

<210> SEQ ID NO 24
<211> LENGTH: 20
<212> TYPE: DNA
<213> ORGANISM: Mus musculus
```

-continued

<400> SEQUENCE: 24
tctccagaaa atcccaacc                                                  20

<210> SEQ ID NO 25
<211> LENGTH: 23
<212> TYPE: DNA
<213> ORGANISM: Mus musculus

<400> SEQUENCE: 25
gctggattgg aagaagatgt att                                             23

<210> SEQ ID NO 26
<211> LENGTH: 19
<212> TYPE: DNA
<213> ORGANISM: Mus musculus

<400> SEQUENCE: 26
ttgaggggaa agtgagacg                                                  19

<210> SEQ ID NO 27
<211> LENGTH: 20
<212> TYPE: DNA
<213> ORGANISM: Mus musculus

<400> SEQUENCE: 27
cttccaccca ggcttcatag                                                 20

<210> SEQ ID NO 28
<211> LENGTH: 20
<212> TYPE: DNA
<213> ORGANISM: Mus musculus

<400> SEQUENCE: 28
tatgggatga ggagcaggac                                                 20

<210> SEQ ID NO 29
<211> LENGTH: 20
<212> TYPE: DNA
<213> ORGANISM: Mus musculus

<400> SEQUENCE: 29
cggataggag acctggacaa                                                 20

<210> SEQ ID NO 30
<211> LENGTH: 19
<212> TYPE: DNA
<213> ORGANISM: Mus musculus

<400> SEQUENCE: 30
actggtgggt ggaatgaca                                                  19

<210> SEQ ID NO 31
<211> LENGTH: 21
<212> TYPE: DNA
<213> ORGANISM: Mus musculus

<400> SEQUENCE: 31
tcaggagggc tcaaagaata a                                               21

<210> SEQ ID NO 32
<211> LENGTH: 19
<212> TYPE: DNA

<213> ORGANISM: Mus musculus

<400> SEQUENCE: 32
gaaagccaag cccaaagac                                                19

<210> SEQ ID NO 33
<211> LENGTH: 20
<212> TYPE: DNA
<213> ORGANISM: Mus musculus

<400> SEQUENCE: 33
gccaacagac tgaggaagga                                               20

<210> SEQ ID NO 34
<211> LENGTH: 19
<212> TYPE: DNA
<213> ORGANISM: Mus musculus

<400> SEQUENCE: 34
acactggcaa ggctggatt                                                19

<210> SEQ ID NO 35
<211> LENGTH: 20
<212> TYPE: DNA
<213> ORGANISM: Mus musculus

<400> SEQUENCE: 35
cgtcctggac aagaccaagt                                               20

<210> SEQ ID NO 36
<211> LENGTH: 20
<212> TYPE: DNA
<213> ORGANISM: Mus musculus

<400> SEQUENCE: 36
attgctgtcc cgaatgtctc                                               20

<210> SEQ ID NO 37
<211> LENGTH: 20
<212> TYPE: DNA
<213> ORGANISM: Mus musculus

<400> SEQUENCE: 37
atcccttacc ctttgccact                                               20

<210> SEQ ID NO 38
<211> LENGTH: 20
<212> TYPE: DNA
<213> ORGANISM: Mus musculus

<400> SEQUENCE: 38
ccgtagcacc tcaatggact                                               20

<210> SEQ ID NO 39
<211> LENGTH: 20
<212> TYPE: DNA
<213> ORGANISM: Mus musculus

<400> SEQUENCE: 39
tgtgagaccg tgctaatgga                                               20

<210> SEQ ID NO 40
<211> LENGTH: 20

<212> TYPE: DNA
<213> ORGANISM: Mus musculus

<400> SEQUENCE: 40
catctccctt cacaaatcgg                                          20

<210> SEQ ID NO 41
<211> LENGTH: 19
<212> TYPE: DNA
<213> ORGANISM: Mus musculus

<400> SEQUENCE: 41
atgggctcct tctccatca                                           19

<210> SEQ ID NO 42
<211> LENGTH: 20
<212> TYPE: DNA
<213> ORGANISM: Mus musculus

<400> SEQUENCE: 42
cctgcttcct cagtctgctc                                          20

<210> SEQ ID NO 43
<211> LENGTH: 20
<212> TYPE: DNA
<213> ORGANISM: Mus musculus

<400> SEQUENCE: 43
ggatctcctg aaggtgctgt                                          20

<210> SEQ ID NO 44
<211> LENGTH: 20
<212> TYPE: DNA
<213> ORGANISM: Mus musculus

<400> SEQUENCE: 44
ttcttttgtg aggccttggt                                          20

<210> SEQ ID NO 45
<211> LENGTH: 20
<212> TYPE: DNA
<213> ORGANISM: Mus musculus

<400> SEQUENCE: 45
cttcagaact gccaaccaca                                          20

<210> SEQ ID NO 46
<211> LENGTH: 20
<212> TYPE: DNA
<213> ORGANISM: Mus musculus

<400> SEQUENCE: 46
gcttctgcca gtgatgctac                                          20

<210> SEQ ID NO 47
<211> LENGTH: 20
<212> TYPE: DNA
<213> ORGANISM: Mus musculus

<400> SEQUENCE: 47
agtcttcact gcccctcatc                                          20

<210> SEQ ID NO 48

```
<211> LENGTH: 20
<212> TYPE: DNA
<213> ORGANISM: Mus musculus

<400> SEQUENCE: 48
tctgtcagtg tggcttctgg                                           20

<210> SEQ ID NO 49
<211> LENGTH: 20
<212> TYPE: DNA
<213> ORGANISM: Mus musculus

<400> SEQUENCE: 49
gtaaatctgc gggatgatgg                                           20

<210> SEQ ID NO 50
<211> LENGTH: 20
<212> TYPE: DNA
<213> ORGANISM: Mus musculus

<400> SEQUENCE: 50
agcagggtca aaatcgtctg                                           20

<210> SEQ ID NO 51
<211> LENGTH: 20
<212> TYPE: DNA
<213> ORGANISM: Mus musculus

<400> SEQUENCE: 51
tgaggtgttc ggtgagattg                                           20

<210> SEQ ID NO 52
<211> LENGTH: 21
<212> TYPE: DNA
<213> ORGANISM: Mus musculus

<400> SEQUENCE: 52
ccatagctca ggtggaagga t                                         21

<210> SEQ ID NO 53
<211> LENGTH: 20
<212> TYPE: DNA
<213> ORGANISM: Mus musculus

<400> SEQUENCE: 53
gagaatccac gaagcctacc                                           20

<210> SEQ ID NO 54
<211> LENGTH: 20
<212> TYPE: DNA
<213> ORGANISM: Mus musculus

<400> SEQUENCE: 54
aatcggacct ctgcctcttt                                           20

<210> SEQ ID NO 55
<211> LENGTH: 20
<212> TYPE: DNA
<213> ORGANISM: Mus musculus

<400> SEQUENCE: 55
tgtcagatga ggaggctgtg                                           20
```

```
<210> SEQ ID NO 56
<211> LENGTH: 20
<212> TYPE: DNA
<213> ORGANISM: Mus musculus

<400> SEQUENCE: 56
ccaggcacga cgtaacttct                                                 20

<210> SEQ ID NO 57
<211> LENGTH: 20
<212> TYPE: DNA
<213> ORGANISM: Mus musculus

<400> SEQUENCE: 57
gggacgtctg ttgagagagc                                                 20

<210> SEQ ID NO 58
<211> LENGTH: 20
<212> TYPE: DNA
<213> ORGANISM: Mus musculus

<400> SEQUENCE: 58
tgtgtccatg gtagcggtaa                                                 20

<210> SEQ ID NO 59
<211> LENGTH: 20
<212> TYPE: DNA
<213> ORGANISM: Mus musculus

<400> SEQUENCE: 59
gcttgccaat ttctcgtctc                                                 20

<210> SEQ ID NO 60
<211> LENGTH: 20
<212> TYPE: DNA
<213> ORGANISM: Mus musculus

<400> SEQUENCE: 60
cttctccttc gccaggttct                                                 20

<210> SEQ ID NO 61
<211> LENGTH: 20
<212> TYPE: DNA
<213> ORGANISM: Mus musculus

<400> SEQUENCE: 61
tgctggtgtg gatattcggg                                                 20

<210> SEQ ID NO 62
<211> LENGTH: 20
<212> TYPE: DNA
<213> ORGANISM: Mus musculus

<400> SEQUENCE: 62
ccttgagatg ggcttatcgg                                                 20

<210> SEQ ID NO 63
<211> LENGTH: 18
<212> TYPE: DNA
<213> ORGANISM: Mus musculus

<400> SEQUENCE: 63
aacgacccct tcattgac                                                   18
```

<210> SEQ ID NO 64
<211> LENGTH: 19
<212> TYPE: DNA
<213> ORGANISM: Mus musculus

<400> SEQUENCE: 64
tccacgacat actcagcac                                              19

<210> SEQ ID NO 65
<211> LENGTH: 20
<212> TYPE: DNA
<213> ORGANISM: Mus musculus

<400> SEQUENCE: 65
cgattctcct ggctgtgaac                                             20

<210> SEQ ID NO 66
<211> LENGTH: 23
<212> TYPE: DNA
<213> ORGANISM: Mus musculus

<400> SEQUENCE: 66
tggaattaac aaaacaagga tgg                                         23

<210> SEQ ID NO 67
<211> LENGTH: 20
<212> TYPE: DNA
<213> ORGANISM: Mus musculus

<400> SEQUENCE: 67
accaaggact tcctatccat                                             20

<210> SEQ ID NO 68
<211> LENGTH: 20
<212> TYPE: DNA
<213> ORGANISM: Mus musculus

<400> SEQUENCE: 68
aggcgatttt ataccaggtt                                             20

<210> SEQ ID NO 69
<211> LENGTH: 20
<212> TYPE: DNA
<213> ORGANISM: Mus musculus

<400> SEQUENCE: 69
caaaaagacc tcgttcagca                                             20

<210> SEQ ID NO 70
<211> LENGTH: 20
<212> TYPE: DNA
<213> ORGANISM: Mus musculus

<400> SEQUENCE: 70
cttcagccat ctgctcttcc                                             20

<210> SEQ ID NO 71
<211> LENGTH: 20
<212> TYPE: DNA
<213> ORGANISM: Mus musculus

<400> SEQUENCE: 71
tgccagagtt tccagacctt                                             20

```
<210> SEQ ID NO 72
<211> LENGTH: 20
<212> TYPE: DNA
<213> ORGANISM: Mus musculus

<400> SEQUENCE: 72
ccaaatgaga caccaaagca                                              20

<210> SEQ ID NO 73
<211> LENGTH: 20
<212> TYPE: DNA
<213> ORGANISM: Mus musculus

<400> SEQUENCE: 73
tctcctgaaa gccaacctca                                              20

<210> SEQ ID NO 74
<211> LENGTH: 20
<212> TYPE: DNA
<213> ORGANISM: Mus musculus

<400> SEQUENCE: 74
ctacgttcca ggatcccaag                                              20
```